(12) United States Patent
Bork

(10) Patent No.: US 10,677,811 B2
(45) Date of Patent: Jun. 9, 2020

(54) SAMPLE RECEPTACLE, SAMPLE CONTAINER AND METHOD OF USE

(71) Applicant: Mastaplex Ltd, Dunedin (NZ)

(72) Inventor: Olaf Bork, Dunedin (NZ)

(73) Assignee: Mastaplex Ltd., Dunedin (NZ)

( * ) Notice: Subject to any disclaimer, the term of this patent is extended or adjusted under 35 U.S.C. 154(b) by 123 days.

(21) Appl. No.: 15/553,902

(22) PCT Filed: Feb. 26, 2016

(86) PCT No.: PCT/NZ2016/050029
§ 371 (c)(1),
(2) Date: Aug. 25, 2017

(87) PCT Pub. No.: WO2016/137342
PCT Pub. Date: Sep. 1, 2016

(65) Prior Publication Data
US 2018/0149670 A1    May 31, 2018

(30) Foreign Application Priority Data

Feb. 27, 2015  (AU) ................................ 2015900695
Dec. 24, 2015  (NZ) ....................................... 715585

(51) Int. Cl.
*G01N 35/00* (2006.01)
*G01N 35/10* (2006.01)
(Continued)

(52) U.S. Cl.
CPC ...... *G01N 35/1009* (2013.01); *B01L 3/50853* (2013.01); *B01L 3/5635* (2013.01);
(Continued)

(58) Field of Classification Search
CPC ................................................ G01N 35/1009
(Continued)

(56) References Cited

U.S. PATENT DOCUMENTS 1,505,599 A    8/1924   Morse
4,626,509 A   12/1986   Lyman
(Continued)

FOREIGN PATENT DOCUMENTS

EP    0297877        1/1989
EP    2058666 A1     5/2009
(Continued)

OTHER PUBLICATIONS

European Search Report for EP Application No. 16 75 5974 dated Jun. 28, 2018, 15 pages.
(Continued)

*Primary Examiner* — Christopher Adam Hixson
*Assistant Examiner* — Emily R. Berkeley
(74) *Attorney, Agent, or Firm* — Merchant & Gould P.C.

(57) ABSTRACT

A sample receptacle including one or more receptacle cavities each having an opening dimensioned such that a liquid within the cavity is retained when the cavity opening is oriented downwardly and/or a gas vent in the base of each cavity sized and positioned to allow gases contained within the cavity to egress whilst preventing the egress of liquid at atmospheric pressure. A sample liquid may be poured into the sample receptacle so that the level of the sample liquid is above each cavity opening and the sample receptacle inverted so as to remove liquid above each cavity whilst retaining sample liquid in each sample receptacle when inverted. This may be used for sample separation or to provide relatively uniform sample volumes to sample wells of a sample container when mated. In another embodiment plungers may be used to eject liquid from receptacle wells via an aperture in the base of each receptacle well.

19 Claims, 12 Drawing Sheets

(51) Int. Cl.
*B01L 3/00* (2006.01)
*G01F 13/00* (2006.01)
*C12Q 1/18* (2006.01)
*G01F 11/26* (2006.01)

(52) U.S. Cl.
CPC ............... *C12Q 1/18* (2013.01); *G01F 13/00* (2013.01); *G01N 35/1072* (2013.01); *G01N 35/1074* (2013.01); *B01L 2300/047* (2013.01); *B01L 2300/048* (2013.01); *B01L 2300/0829* (2013.01); *B01L 2400/0457* (2013.01); *B01L 2400/0478* (2013.01); *G01F 11/262* (2013.01)

(58) Field of Classification Search
USPC .......................................................... 436/180
See application file for complete search history.

(56) References Cited

U.S. PATENT DOCUMENTS

| | | | |
|---|---|---|---|
| 5,869,158 A | 2/1999 | Smith | |
| 7,592,185 B2 | 9/2009 | Karg et al. | |
| 8,739,608 B2 | 6/2014 | Wilson | |
| 8,906,310 B2 | 12/2014 | Bonecker | |
| 9,175,333 B2 | 11/2015 | Young et al. | |
| 9,180,461 B2 | 11/2015 | Edens et al. | |
| 2002/0137199 A1 | 9/2002 | Jobin et al. | |
| 2003/0204331 A1 | 10/2003 | Whitney et al. | |
| 2004/0141885 A1 | 7/2004 | Godin et al. | |
| 2004/0203174 A1 | 10/2004 | Jones et al. | |
| 2004/0230174 A1 | 10/2004 | Jones et al. | |
| 2005/0029308 A1 | 2/2005 | Benett et al. | |
| 2006/0009713 A1 | 1/2006 | Flaherty | |
| 2006/0024211 A1 | 2/2006 | Giter et al. | |
| 2009/0088336 A1 | 4/2009 | Burd | |
| 2011/0009717 A1 | 1/2011 | Davis et al. | |
| 2014/0256598 A1 | 9/2014 | Derosier | |
| 2015/0126904 A1 | 5/2015 | Calderwood et al. | |

FOREIGN PATENT DOCUMENTS

| | | |
|---|---|---|
| WO | 2007068951 | 6/2007 |
| WO | 2008002562 A2 | 1/2008 |
| WO | 2009022312 | 2/2009 |

OTHER PUBLICATIONS

International Search Report for International Application No. PCT/NZ2016/050029 dated Jun. 16, 2016 (6 pages).
International Written Opinion for International Application No. PCT/NZ2016/050029 dated Jun. 16, 2016 (8 pages).
International Report on Patentability for International Application No. PCT/NZ2016/050029 dated Jun. 16, 2016 (24 pages).

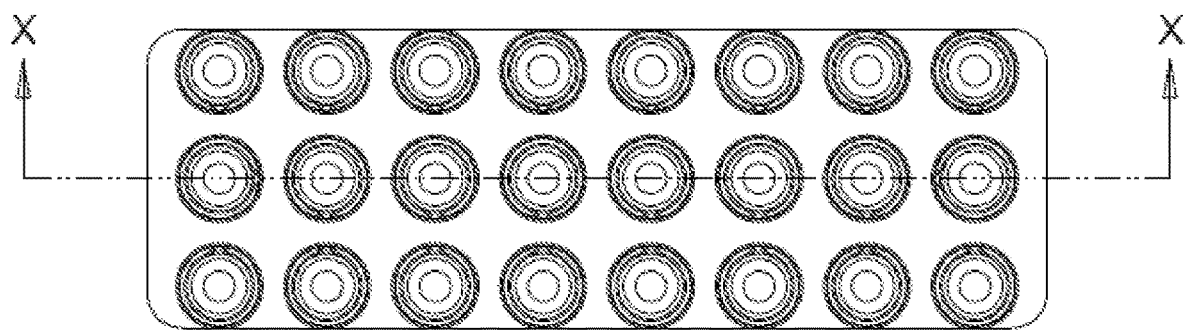
Figure 13
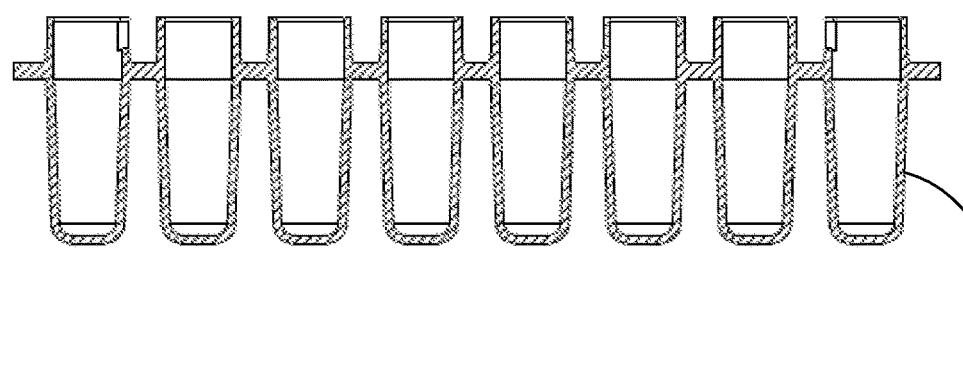
Figure 14     18

SAMPLE RECEPTACLE, SAMPLE CONTAINER AND METHOD OF USE

This application is a National Stage Application of PCT/NZ2016/050029, filed 26 Feb. 2016, which claims benefit of Serial No. 2015900695, filed 27 Feb. 2015 in Australia and 715585, filed 24 Dec. 2015 in New Zealand and which applications are incorporated herein by reference. To the extent appropriate, a claim of priority is made to each of the above disclosed applications.

FIELD

This invention relates to a sample receptacle for providing a desired volume of a sample liquid. It may be used to provide liquid samples of relatively constant volume to wells of a microplate containing a range of reactants of different concentrations for sample liquid analysis or in a range of other applications.

BACKGROUND

In a range of liquid testing applications a number of samples of consistent volume need to be analysed—such as in multiplex assays, biological liquid analysis including antibiotic susceptibility testing, for example using the micro dilution method (such as used for bacteria isolated from mastitis milk), and chemical residue testing.

A range of techniques are currently employed to deliver liquid samples of a consistent volume for laboratory analysis. The common method of pipetting a liquid can provide very accurate liquid volumes but requires experience and skill to achieve consistent results and is time consuming. Further, the orifice of the pipette is of limited diameter—which can make it difficult to pipette biological samples such as clotted milk.

Small capillary tubes may be used to transfer small volumes of liquid but these are difficult to use and do not allow the simultaneous acquisition of a number of samples of constant and sufficient volume for typical laboratory processing.

A range of automated dispensing systems are available but these may be too expensive, complex or bulky for small scale analysis.

It is an object of the invention to provide a relatively simple and inexpensive sample receptacle capable of providing relatively consistent sample volumes or to at least provide the public with a useful choice.

SUMMARY

According to one example embodiment there is provided a sample receptacle having:
 a. a base;
 b. one or more receptacle walls extending from the base to define an enclosed region; and
 c. one or more receptacle cavities each having an opening located within the enclosed region, each cavity opening being positioned below the one or more walls and having an opening dimensioned such that a liquid within the cavity is retained when the cavity opening is oriented downwardly.

According to another example embodiment there is provided a sample receptacle including one or more receptacle cavities, each cavity having a gas vent in its base sized and positioned to allow gases contained within the cavity to egress whilst preventing the egress of liquid.

According to a further example embodiment there is provided a sample container including one or more sample wells each having a mouth for receiving a liquid wherein each mouth has a slot to facilitate mating with the mouth of a receptacle.

According to another example embodiment there is provided a sample receptacle having:
 a. a base;
 b. one or more receptacle walls extending from the base to define an enclosed region; and
 c. a plurality of receptacle cavities located within the enclosed region, each cavity having:
  i. a cavity opening positioned below the one or more walls being sized such that a liquid within the cavity is retained when the cavity opening is oriented downwardly; and
  ii. a vent from the cavity dimensioned to permit the egress of gas but prevent the egress of liquid.

According to a still further example embodiment there is provided a method of providing a desired liquid sample volume to one or more sample containers comprising the steps of:
 a. providing a sample receptacle having:
  i) a base,
  ii) one or more receptacle walls extending from the base to define an enclosed region; and
  iii) one or more receptacle cavities each having an opening located within the enclosed region, each cavity opening being positioned below the one or more walls and having an opening dimensioned such that a liquid within the cavity is retained when the cavity opening is oriented downwardly;
 b. introducing a sample liquid into the sample receptacle so that the level of the sample liquid is above each cavity opening;
 c. inverting the sample receptacle so as to remove excess sample liquid whilst retaining sample liquid in each sample receptacle when inverted;
 d. mating each sample container with each respective cavity to form a liquid tight connection; and
 e. applying a dislodging force to release sample liquid from each cavity into each sample container.

According to a further aspect there is provided a sample analysis kit comprising:
 a. a sample receptacle including one or more receptacle wells, each well having one or more apertures in its base;
 b. a sample container including one or more container wells each having a mouth dimensioned to mate with the base of a respective receptacle well; and
 c. a plunger assembly including one or more pistons dimensioned to advance within a respective receptacle well so as to eject liquid within the receptacle well out of each aperture.

According to a further aspect there is provided a method of sample analysis utilising a sample analysis kit as described above comprising the steps of:
 a. filling each receptacle well with fluid;
 b. mating the plunger assembly with the sample receptacle so that a plunger is introduced into the mouth of each receptacle well; and
 c. advancing the plunger towards the sample receptacle so that fluid within each receptacle well is ejected through each aperture into each respective container well.

According to a further aspect there is provided a method of separating components of a sample comprising the steps of:
  a. providing a sample receptacle having:
    i) a base,
    ii) one or more receptacle walls extending from the base to define an enclosed region; and
    iii) one or more receptacle cavities each having an opening located within the enclosed region, each cavity opening being positioned below the one or more walls and having an opening dimensioned such that a liquid within the cavity is retained when the cavity opening is oriented downwardly;
or including:
  one or more receptacle cavities, each cavity having a gas vent in its base sized and positioned to allow gases contained within the cavity to egress whilst preventing the egress of liquid at atmospheric pressure;
  b. introducing a sample liquid into the sample receptacle so that the level of the sample liquid is above each cavity opening;
  c. allowing the sample to settle into different sample layers; and
  d. inverting the sample receptacle so as to remove a surface sample layer whilst retaining sample liquid in each sample receptacle when inverted.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e., they will be taken to mean an inclusion of the listed components which the use directly references, and possibly also of other non-specified components or elements. Reference to any document in this specification does not constitute an admission that it is prior art, validly combinable with other documents or that it forms part of the common general knowledge.

BRIEF DESCRIPTION OF THE DRAWINGS

The accompanying drawings which are incorporated in and constitute part of the specification, illustrate embodiments of the invention and, together with the general description of the invention given above, and the detailed description of embodiments given below, serve to explain the principles of the invention, in which:

FIG. 13 is a top view of the sample container shown in FIG. 11;

FIG. 14 is a cross-sectional view along line X-X of the sample container shown in FIG. 13;

DETAILED DESCRIPTION

Figure 1:
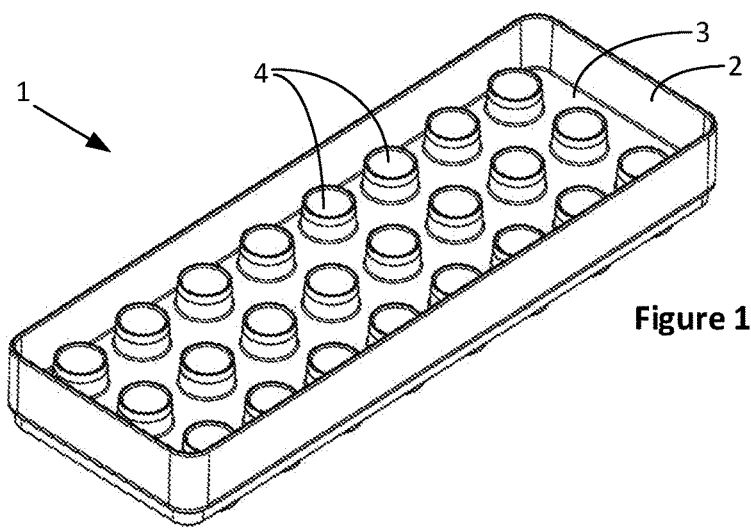
FIG. 1 is a top perspective view of a sample receptacle according to one embodiment.
Figure 2:
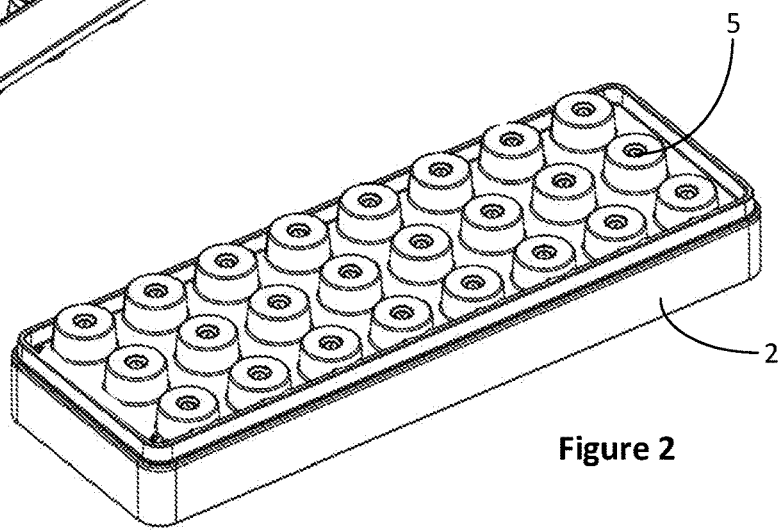
FIG. 2 is a bottom perspective view of the sample receptacle shown in FIG. 1.
Figure 3:
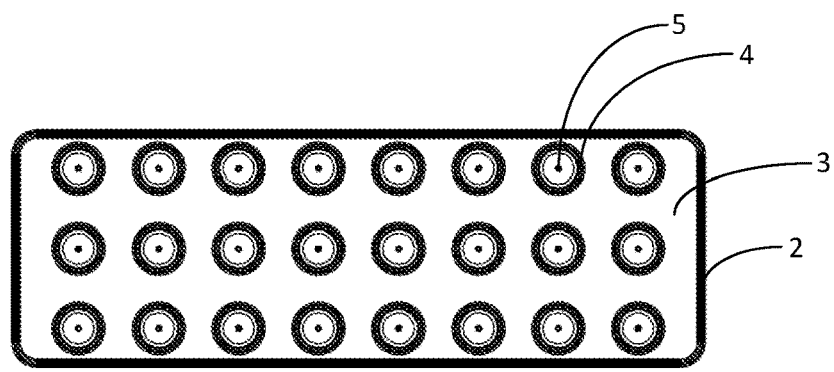
FIG. 3 is a bottom view of the sample receptacle shown in FIG. 1.
Figure 4:
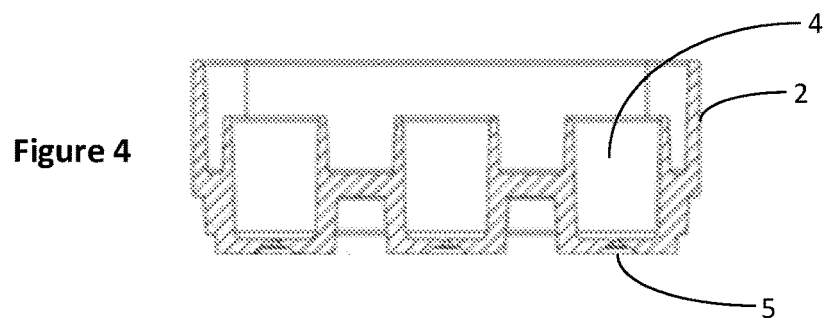
FIG. 4 is a cross-sectional view of the sample receptacle shown in FIG. 1.

The following description describes a sample receptacle and sample container and associated method suitable for the analysis of mastitis in milk. However, it is to be appreciated that the invention is not limited to this application and may be used to provide liquid samples of a desired volume in a wide variety of applications. Whilst these applications may include a wide range of laboratory and non-laboratory sample analysis applications the invention has particular application in relation to the analysis of biological samples such as milk, urine, blood, sputum, diluted faecal matter and tissue liquids. It may also be used in the analysis of water samples from lakes, rivers and the sea; water samples from wastewater plants; and aqueous and non-aqueous samples from industry, particularly the food industry. The sample receptacle and method may also find application for sample separation. In some applications it is desirable to remove floating particles, debris, fats or oils from a sample. In other cases the floating material may be the desired sample material. Potential applications include the removal of wanted or inhibitory substances for particle analysis, ELISA or DNA analysis such as polymerase chain reaction (PCR) or isothermal DNA amplification.

FIGS. 1 to 4 show a sample receptacle 1 having a receptacle wall 2 surrounding a base 3 with a plurality of cavities 4 formed in the base. The receptacle wall is preferably greater than 1 mm higher than cavity openings, and more preferably greater than 3 mm, and even more preferably greater than 6 mm.

Whilst a single cavity could be provided, an array of cavities is advantageous for multi-sample analysis. The cavities are preferably arranged in a regular array and arranged to mate with wells of a standard microplate such as defined in the ANSI SLAS 4-2004 (R2012) standard (formerly recognized as ANSI/SBS 4-2004). Preferred arrays are the standard 96 or 384 well plate arrays or 8, 24 or 48 well strip arrays.

In use a liquid is introduced into the region of the sample receptacle bounded by wall 2 when upright (the orientation shown in FIG. 1) to a level above that of the cavity openings. This allows all cavities 4 to be filled in one simple imprecise pouring operation. When small cavities are filled with certain liquids (such as blood, urine, milk and water) air pockets may form. This is believed to be due to the manner in which liquid is introduced into the cavities and cohesive forces (surface tension) of the liquid forming a bridge which prevents the liquid filling the cavities. In addition, physico-chemical properties of such liquids may be unfavourable to allow wetting of the sample receptacle. For a small sample the gravitational forces acting upon the liquid are too weak to overcome the bridge.

In the embodiment shown in FIGS. 1 to 4 the base of each cavity is provided with a gas vent 5 of small cross-sectional area (in this case circular) to allow gas trapped within the cavity to vent. If the sample receptacle is filled with liquid and left to rest for a period the force of gravity upon the liquid and the gas venting path allows a substantial proportion of the entrapped gas to be released.

The gas vent may be suitably sized and positioned to allow gases contained within the cavity to egress whilst preventing the egress of liquid. The ideal size will depend upon the sample liquid and material that the receptacle is formed of.

The gas vent is preferably in the form of an opening in the base of each cavity or in a side wall of each cavity located towards the base. The gas vent preferably has a cross-sectional area of less than 1 mm$^2$, and preferably less than 0.5 mm$^2$, and more preferably less than 0.25 mm$^2$ and even more preferably less than 0.1 mm$^2$. Where the gas vent has a circular cross-section this equates to a diameter of less than 0.8 mm, more preferably less than 0.6 mm and even more preferably less than 0.45 mm. With such venting for liquids such as blood, urine, milk and water consistent volumes may be obtained with a coefficient of variation in volume typically less than 10%.

In other embodiments no gas vents will be provided as for some liquids, such as organic solvents, for example ethanol, and oils for example medium chain triglyceride, more consistent volumes are delivered from each cavity when no vent is provided. It is believed that such liquids are less prone to formation of blocking bridges and the vents simply serve to leak a portion of the sample from the cavity. For certain liquids, such as ethanol and triglyceride more consistent volumes may be delivered without venting and with venting the coefficient of variation of sample volume may exceed 35%.

If the sample receptacle is inverted excess liquid retained within receptacle wall 2 above and between the cavities 4 may be removed whilst liquid within the cavities 4 may be retained as will be described. Once liquid is filled into the cavities and the receptacle is held upside down, the liquid remains in the cavities due to adhesive and cohesive forces acting on the liquid if the cavity dimensions are appropriately selected. Adhesive forces apply between the liquid and the cavity wall and cohesive forces between liquid molecules. The gravitational forces are too weak to overcome the adhesive and cohesive forces without an additional force such as shaking or tapping the receptacle to release the liquid from the cavities.

Where each cavity is a continuous cylindrical cavity and the opening is circular in cross-section the cavity diameter is preferably of a diameter of between 1 mm and 15 mm, more preferably between 2 mm and 10 mm, more preferably between 2 mm and 7 mm and even more preferably between 3 mm and 6 mm. The cavity opening may be of a smaller cross-sectional area than the cavity cross-sectional area. This may be advantageous where a large sample volume is desired. The opening may be in the form of a tapered opening or a lip defining an aperture of desired shape—e.g. circular, rectangular or triangular. The cross-sectional area of the opening is preferably less than 100 mm$^2$ and more preferably less than 64 mm$^2$.

Taking the above design considerations into account each cavity is to be dimensioned such as to retain liquid within the cavity when inverted and to release liquid retained in the cavity when the cavity opening is oriented downwardly and a dislodging force (such as a tap or shaking) is applied. The cavity height is preferably between 0.5 mm to 20 mm, more preferably between 2 mm to 7 mm. The volume of each cavity is preferably between 0.8 ul to 1 ml.

Figure 5:
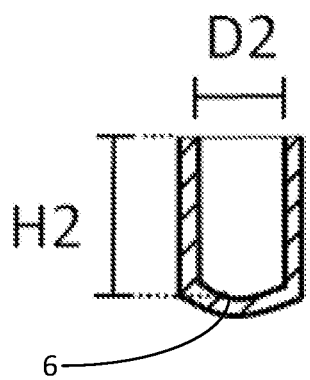
FIGS. 5-10 show sample receptacle cavity profiles according to a number of embodiments.
Figure 6:
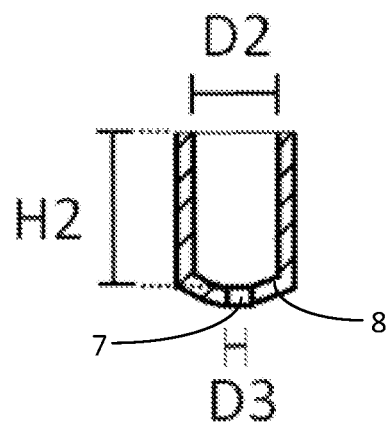
Figure 7:
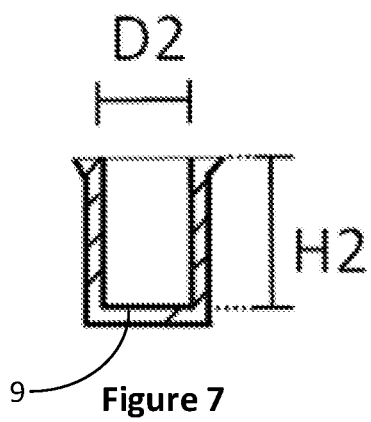
Figure 8:
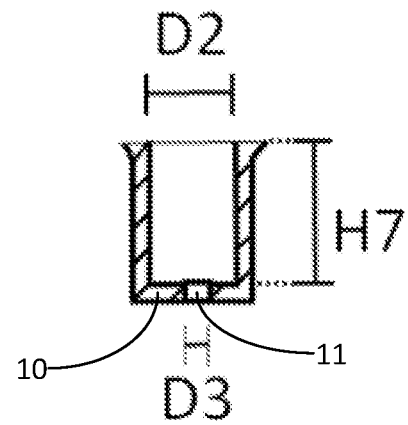
Figure 9:
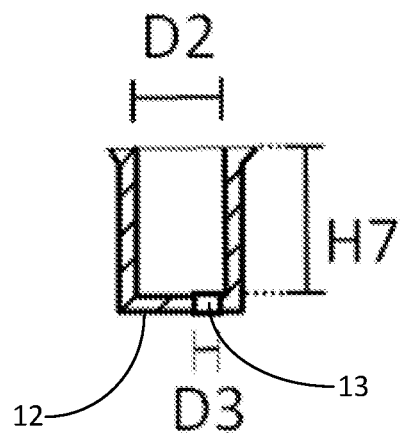
Figure 10:
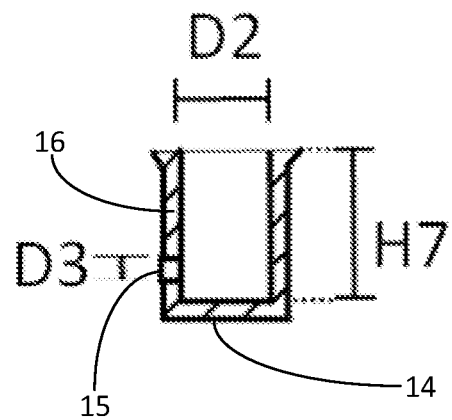
Figure 11:
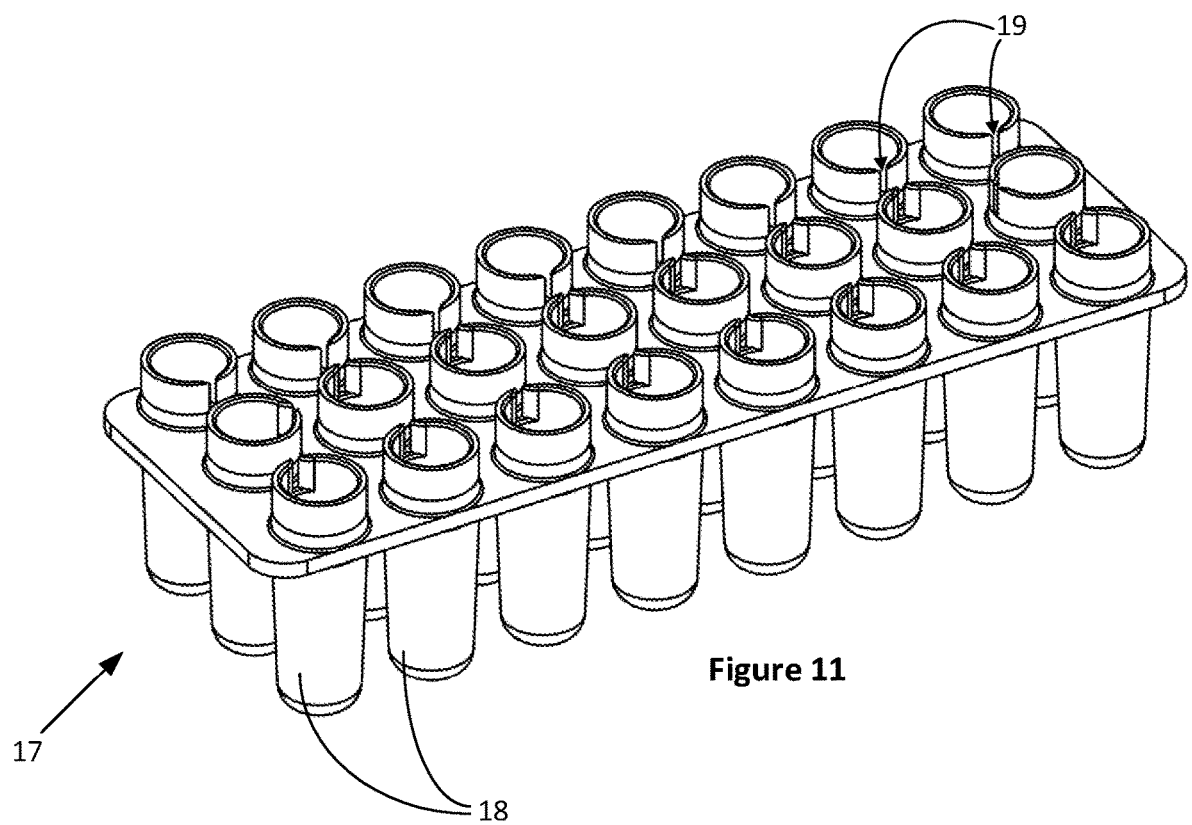
FIG. 11 is a top perspective view of a sample container according to one embodiment.
Figure 12:
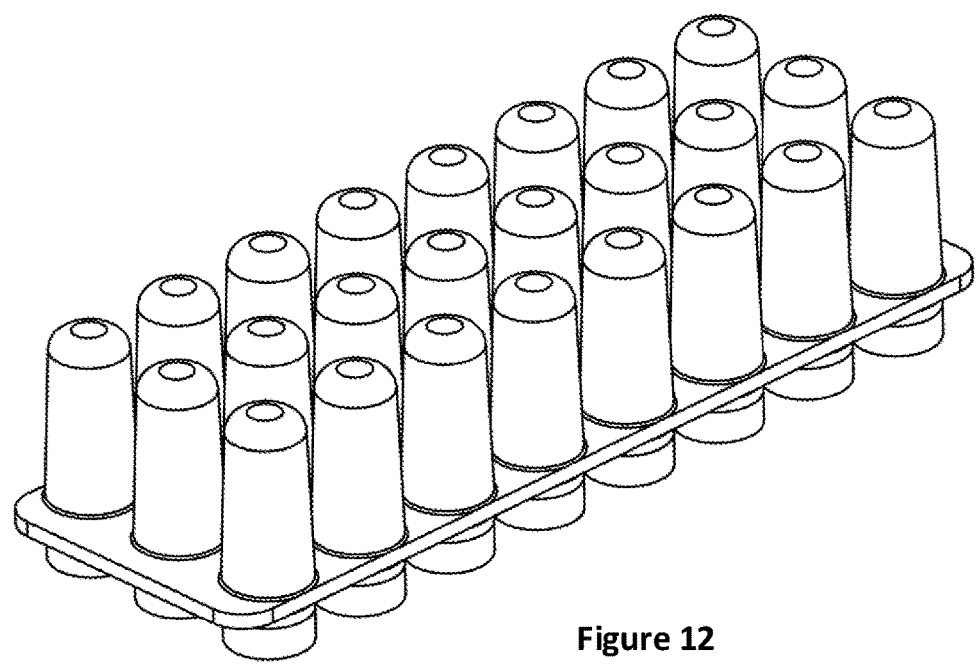
FIG. 12 is a bottom perspective view of the sample container shown in FIG. 11.

Referring to FIGS. 5 to 10 a range of cavity profiles are shown. FIG. 5 shows a cavity of height H2 and diameter D2 with a curved or semi-spherical base 6. FIG. 6 shows a cavity of height H2 and diameter D2 having a curved or semi-spherical base 8 with a centrally located vent hole 7 of diameter D3. FIG. 7 shows a cavity of height H2 and diameter D2 having a flat base 9. FIG. 8 shows a cavity of height H7 and diameter D2 having a flat base 10 and centrally located gas vent 11 of diameter D3. FIG. 9 shows a cavity of height H7 and diameter D2 having a flat base 10 and an off-centre gas vent 11 of diameter D3. FIG. 10 shows a cavity of height H7 and diameter D2 having a flat base 14 and a gas vent 15 of diameter D3 through side wall 16.

The sample receptacle is preferably formed of a thermoplastics material. Preferred thermoplastics materials include Acrylic, poly(methyl methacrylate), ABS (Acrylonitrile butadiene styrene), Nylon, PLA, Polylactic acid, Polybenzimidazole, Polycarbonate, Polyether sulfone, Polyetherether ketone, Polyetherimide, Polyethylene, Polyphenylene oxide, Polyphenylene sulfide, Polypropylene, Polystyrene, Polyvinyl chloride and Teflon. Particularly preferred materials include Polypropylene, Polyethylene, Polystyrene and ABS. Most preferred is Polypropylene.

FIGS. 11 to 14 show a sample container suitable for use with the sample receptacle shown in FIGS. 1 to 4. The sample container 17 has a plurality of wells 18 dimensioned and arranged so as to mate with a corresponding sample receptacle. The mouths of each well have a slot 19 which has two purposes. Firstly it allows a certain amount of deformation of the mouth of each well of the sample container to facilitate mating with each respective cavity of the sample receptacle. Secondly, when mated, the slot provides a gas vent to facilitate the transfer of liquid from the sample receptacle cavities to the wells of the sample container.

The wells 18 are preferably arranged in a regular array such as defined in the ANSI SLAS 4-2004 (R2012) standard (formerly recognized as ANSI/SBS 4-2004). Preferred arrays are the standard 96 or 384 well plate arrays or 8, 24 or 48 well strip arrays. Each sample well is preferably capable of holding a volume of liquid between 1 ul to 2000 ul, more preferably 10 ul to 1000 ul, and even more preferably 20 ul to 500 ul.

Figure 15:
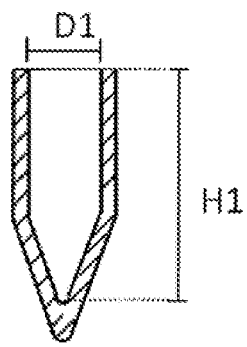
FIG. 15-17 show sample container well profiles according to a number of embodiments.
Figure 16:
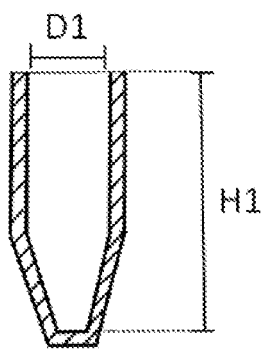
Figure 17:
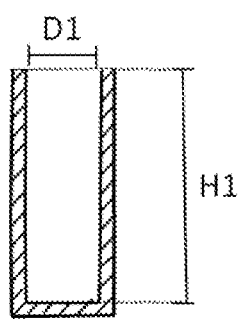

FIGS. 15 to 17 show a range of sample well shapes of diameter D1 and height H1. Where each well has a circular cross section its diameter is preferably between 1 mm to 10 mm. The well height is preferably between 2 mm to 50 mm. The base of each well may be conical as shown in FIG. 15, Frusto-conical as shown in FIG. 16, flat as shown in FIG. 17 or hemisperical as shown in FIG. 20.

Figure 18:
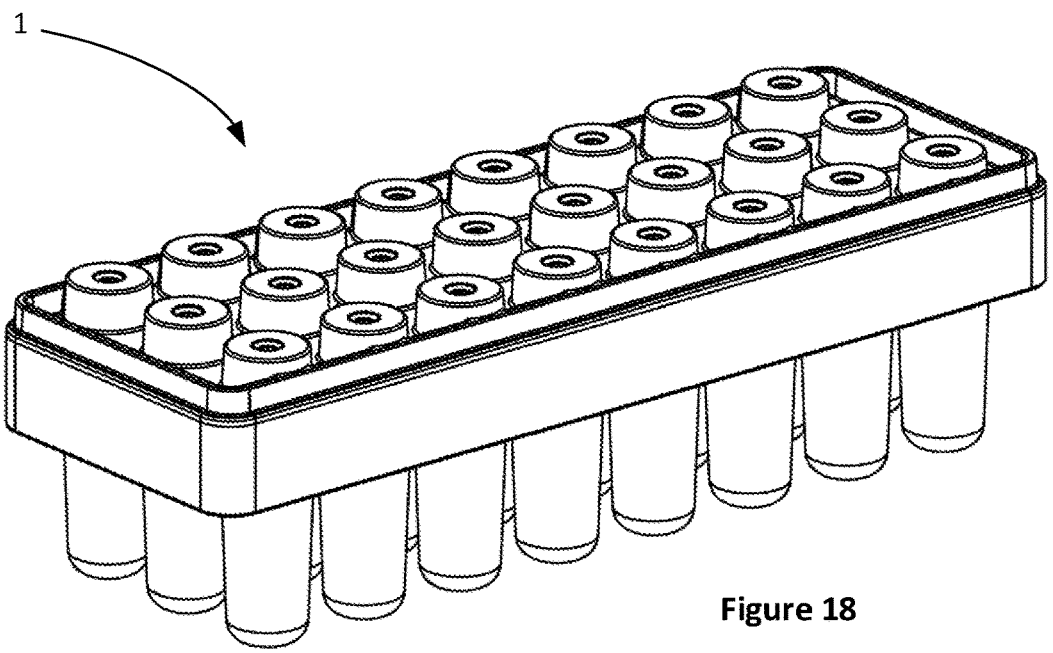
FIG. 18 is a top perspective view of the sample receptacle of FIG. 1 mated with the sample container of FIG. 11.
Figure 19:
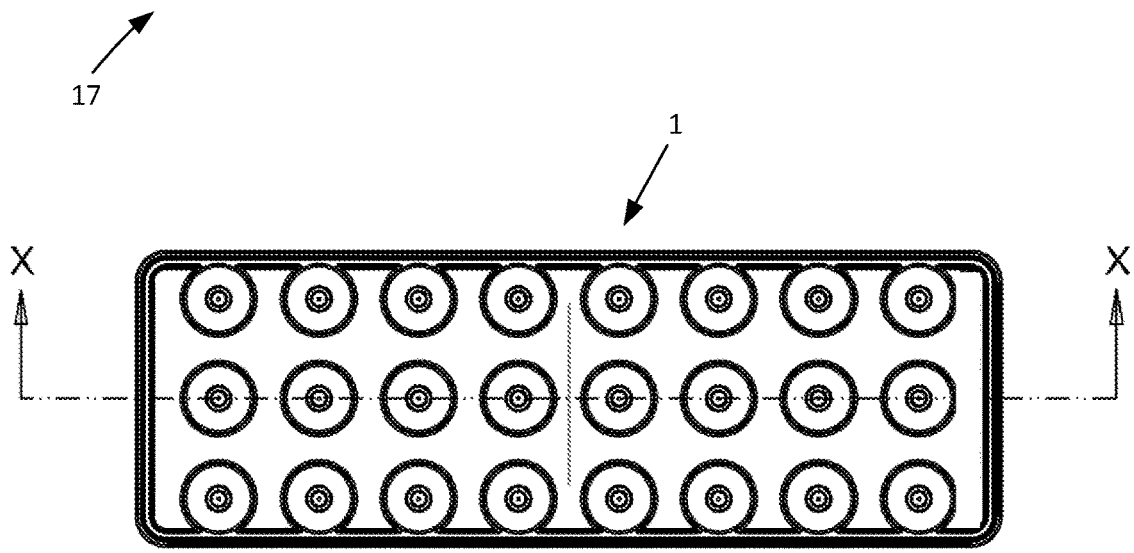
FIG. 19 is a top view of the mated components shown in FIG. 18.
Figure 20:
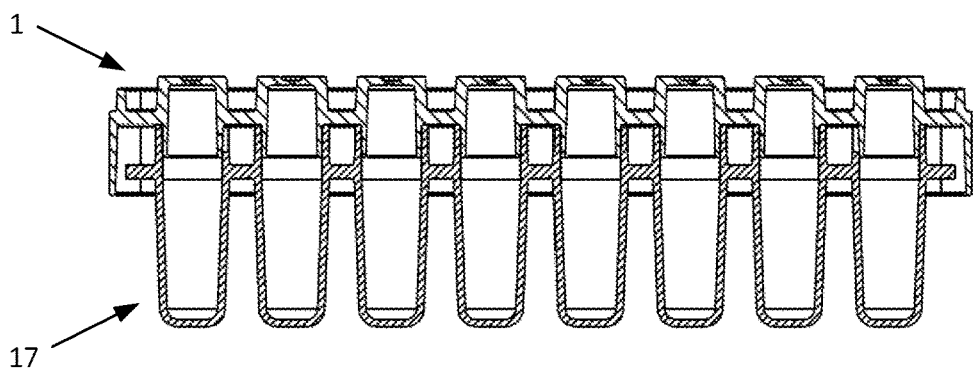
FIG. 20 is a cross-sectional view along line X-X of the mated components shown in FIG. 18.
Figure 21:
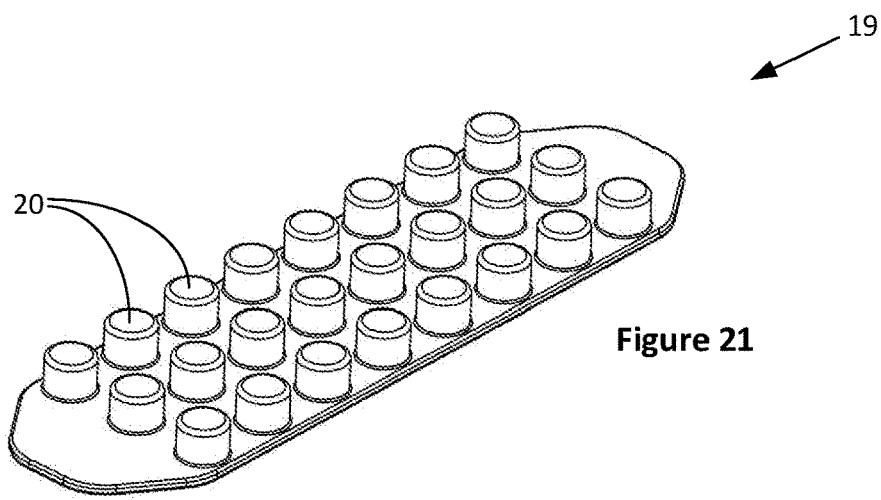
FIG. 21 is a bottom perspective view of a mat for sealing the wells of a sample container.
Figure 22:
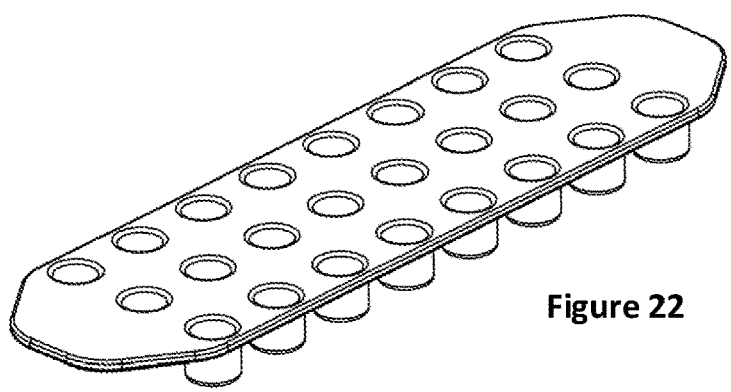
FIG. 22 is a top perspective view of the mat shown in FIG. 21.

FIGS. 18 to 20 show the sample receptacle and sample container in use when mated together. In use a sample liquid is poured or otherwise introduced into the region defined by receptacle wall 2 to a level above the cavity openings (see orientation in FIG. 1). Depending upon the sample liquid, the liquid may or may not be left in the receptacle to settle. In the case of a milk sample a gas vent is provided and the sample is left to rest for a period for the gas in the liquid to egress through the gas vent.

The receptacle is then inverted so that the cavity openings of the sample receptacle face downwardly. The liquid within the receptacle wall above and between the cavities drops away whilst liquid within the cavities is retained. The inverted sample receptacle is then mated with the sample container as shown in FIGS. 18 to 20. At this stage the liquid samples are still retained within each cavity with respective cavities and wells mated together forming a liquid tight connection. A dislodging force in the form of a tap to the base of the sample receptacle or shaking may release sample liquid from each cavity into each well of the sample container.

In some applications instead of providing a gas vent it may be feasible to provide a column of liquid above each cavity of such height that the hydrostatic pressure of the liquid acting upon the liquid in the cavities expels trapped gasses. This would require a sample receptacle of larger dimensions though.

Advantageously at least some of the wells of the sample container may be prefilled with one or more reactant. When testing for mastitis the wells may be pre-filled with bacteria culture media, dyes and a number of antibiotics, each in a range of different concentrations such as an antibiotic dilution series of 512 ug/ml, 256 ug/ml, 128 ug/ml, 64 ug/ml, 32 ug/ml, 16 ug/ml, 8 ug/ml, 4 ug/ml, 2 ug/ml, 1 ug/ml, 0.5 ug/ml, 0.25 ug/ml, 0.125 ug/ml, 0.0625 ug/ml, 0.032 ug/ml, 0.016 ug/ml. Other concentrations may of course be used depending upon the application.

Dyes such as pH dyes, redox dyes, metabolic dyes, fluorescent dyes, bacteria culture media, and antimicrobials including antibiotics may also be pre-supplied to each well as a solid or liquid.

Once the reactants (solid or liquid) are pre-supplied to wells, the sample container 17 may be closed with a mat 19 having a plurality of stoppers 20. Once the predetermined volume of sample liquid is supplied to each well (which may contain a desired concentration of a reactant, dye, culture media etc.) the mat will be removed from the sample container and the sample container and sample receptacle mated with the sample liquid released from each cavity into each respective well.

Figure 23:
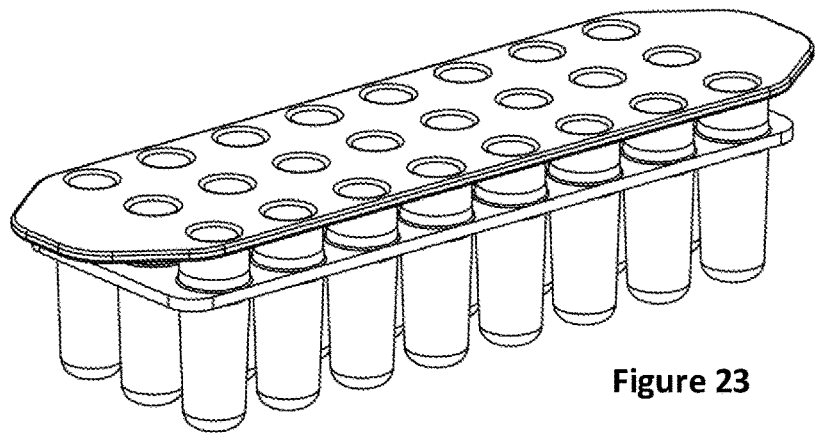
FIG. 23 is a top perspective view of a mat as shown in FIG. 21 mated with a sample container as shown in FIG. 11.
Figure 24:
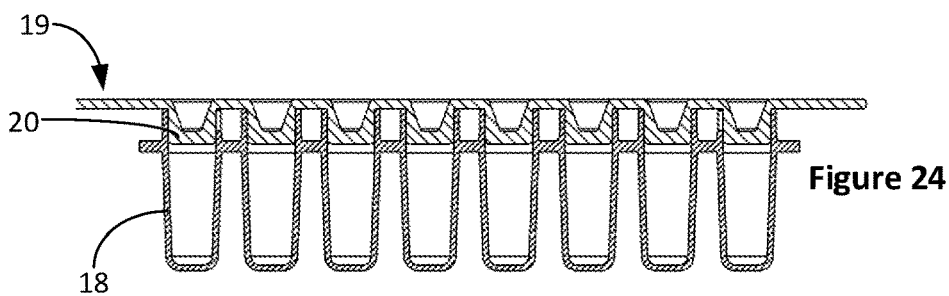
FIG. 24 is a cross-sectional view of the mated sample container and mat shown in FIG. 23.

Once the predetermined volume of sample liquid is supplied to each well the sample receptacle 1 may be removed and stoppers 20 of mat 19 may be mated with the mouths of the respective receptacles as shown in FIGS. 23 and 24. If required the samples and reactants may be incubated for an appropriate period of time. After incubation the wells may be analysed—suitably by an optical reader sensitive to the relevant spectrum for any dyes employed. The reader may also read a code applied to the sample container such as a bar code. This approach could of course be adapted for an automated system too.

It has been found that the sample receptacle described above is able to deliver very consistent sample volumes independent of user skill and with the results varying little between users as shown in the examples at the end of this specification. This makes this approach particularly attractive for applications such as on farm mastitis detection in milk samples. A farm worker and/or veterinarian is able to simply and quickly obtain multiple samples of a required volume to perform one or more analyses without requiring special skill or training.

Whilst the above description is directed to the use of the receptacle to deliver a relatively constant volume of sample fluid to the wells of a sample container the receptacle may be used alone for sample separation. If a sample liquid is introduced into the receptacle to a level above the openings of the receptacle cavities and allowed to settle for a suitable time then the sample liquid may separate into layers—e.g. oil, fat, debris etc. may float to the top. The top layer above the cavities may be removed by inverting the receptacle and either the removed liquid may be utilised as a sample or the liquid remaining in the cavities may be used as a sample.

There is thus provided a sample receptacle capable of quickly delivering multiple samples of uniform sample volumes with low standard deviation that requires little skill to use. The device is simple, effective and inexpensive and enables cost effective and timely on farm mastitis management.

Figure 30:
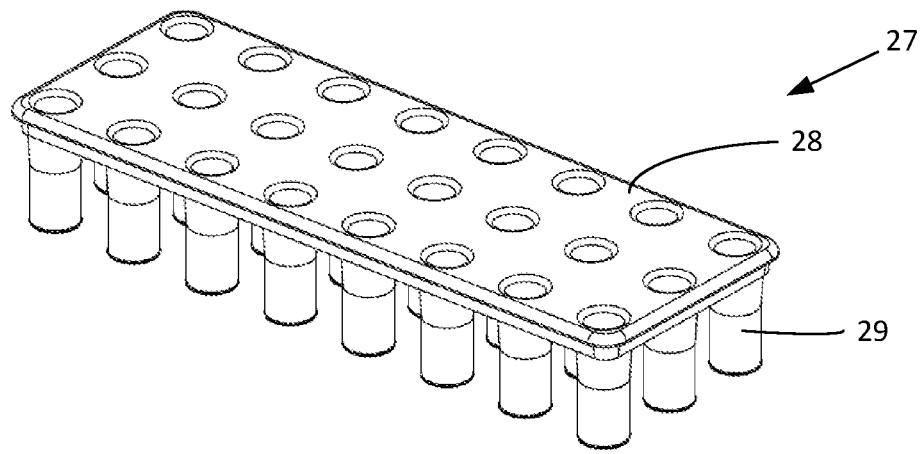
FIG. 30 is a top perspective view of a plunger assembly according to one embodiment.
Figure 31:
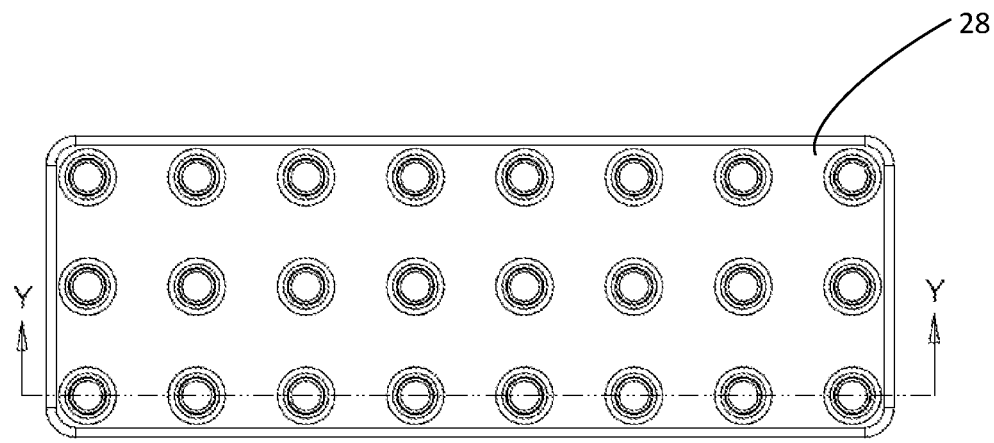
FIG. 31 is a top view of the plunger assembly shown in FIG. 30.
Figure 32:
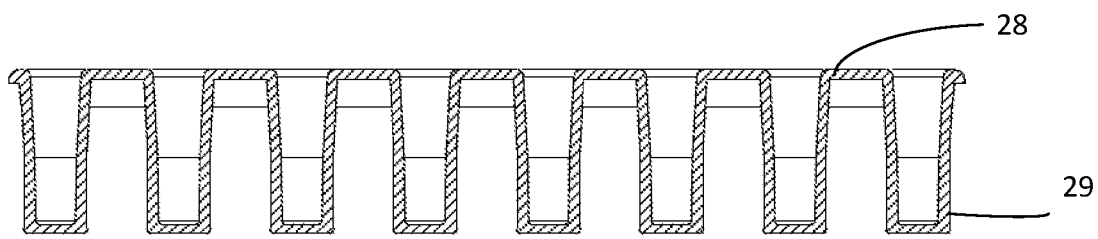
FIG. 32 is a cross-sectional view along line X-X of the plunger assembly shown in FIG. 31.
Figure 33:
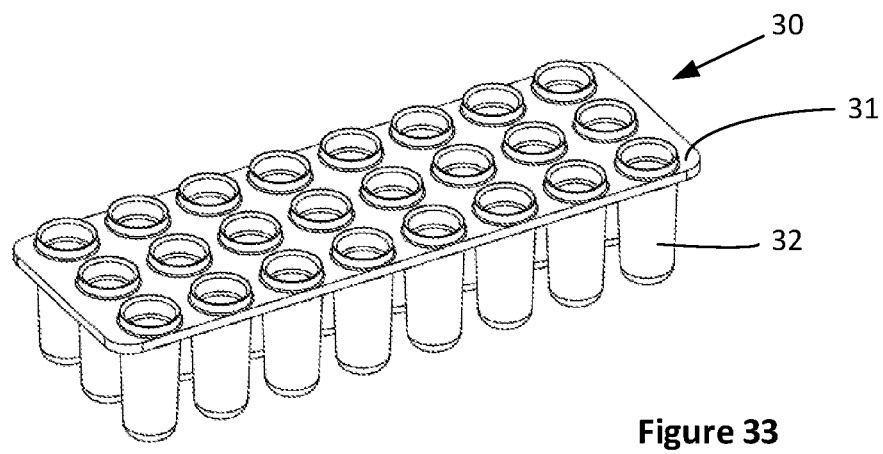
FIG. 33 is a top perspective view of the sample container according to a further embodiment.
Figure 34:
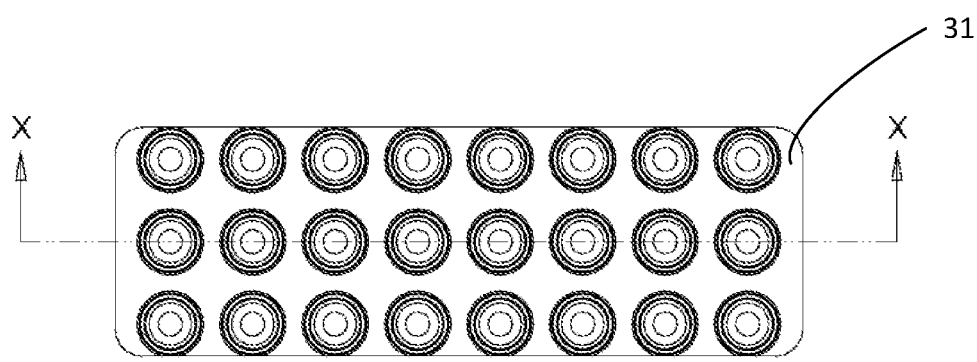
FIG. 34 is a top view of the sample container shown in FIG. 33.
Figure 35:
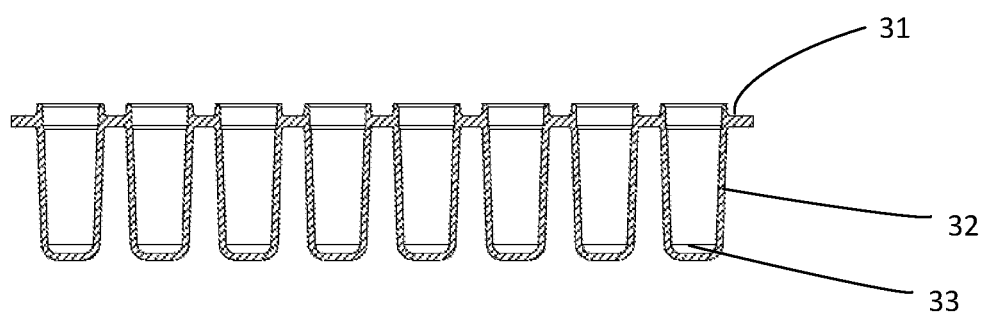
FIG. 35 is a cross-sectional view along line X-X of the sample container shown in FIG. 34.

Referring now to FIGS. 25 to 39 a sample analysis kit according to a further embodiment will be described. The sample analysis kit includes a sample receptacle as shown in FIGS. 25 to 29 that may be mated with the sample container as shown in FIGS. 33 to 35 and a plunger assembly as shown in FIGS. 30 to 32 that may force liquid out of the receptacle wells.

Figure 25:
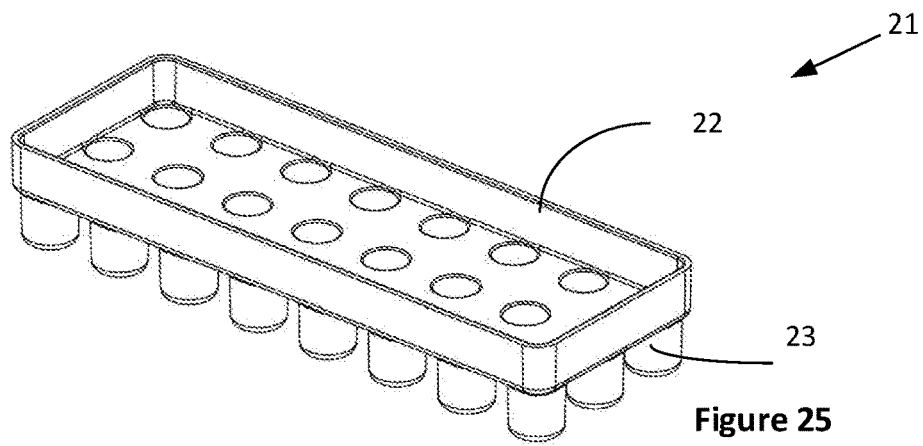
FIG. 25 is a top perspective view of a sample receptacle according to a further embodiment.
Figure 26:
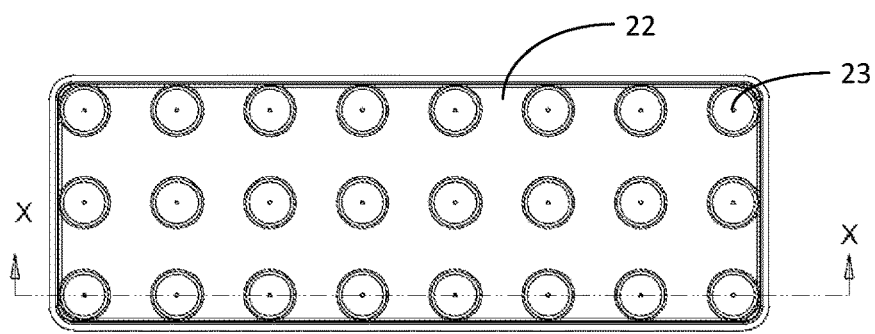
FIG. 26 is a top view of the sample receptacle shown in FIG. 25.
Figure 27:
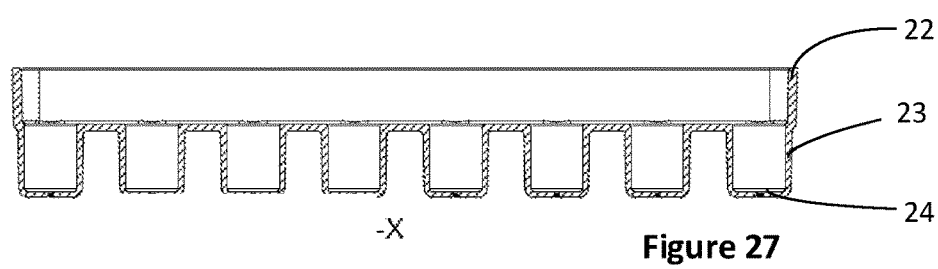
FIG. 27 is a cross-sectional view of the sample receptacle shown in FIGS. 25 and 26.

Referring to FIGS. 25 to 27 sample receptacle 21 includes a plurality of receptacle wells 23 surrounded by a receptacle wall 22. Each receptacle well 23 has one or more apertures 24 in its base. As shown in FIG. 27 a single aperture 24 may be provided in the base of each receptacle well 23. As in the previous embodiments this will function as a gas vent and so should be sized as per the previous embodiments.

Figure 28:
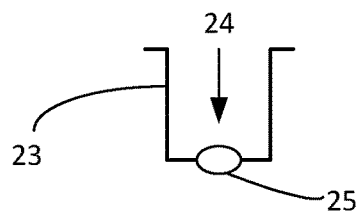
FIG. 28 shows sample receptacle cavity with its vent sealed by gel.

In the embodiment shown in FIG. 28 each aperture is sealed by a displaceable seal—in this case gel 25 seals aperture 24. Each aperture could also be sealed by wax or similar material a melting point in a desired range (i.e. 35 C or 50 C) which melts and then releases the media from cavity into the well. In this case the venting hole could be much larger (several millimeters) so that gravitational forces only may release the liquid from the cavity into the well. Such a larger aperture may also allow for easier transfer of clotted or more viscous material. Such a seal may also retain and protect reactants within sample wells when a sample receptacle is mated with a sample container as described below. Whilst gel is given as an example the seal could be a thin layer adhered to the base of each receptacle well or a solid element inserted in each aperture etc.

Figure 29:
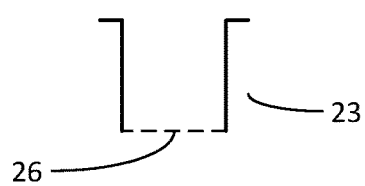
FIG. 29 shows sample receptacle cavity having a plurality of perforations in its base.

In the embodiment shown in FIG. 29 a plurality of apertures are provided by a perforated element 26 (such as a filter) provided at the base of each well 23. Each aperture of the perforated element would need to be sized to avoid the egress of fluid under normal atmospheric pressure. However, when each receptacle well 23 is pressurised this would provide a greater number apertures to assist the transfer of liquid to the sample wells. This may also be useful to separate out particles above a desired size. This feature could also be incorporated in the previous embodiments.

FIGS. 30 to 32 show a plunger assembly 27 consisting of a base 28 with a plurality of pistons 29 projecting therefrom. The pistons 29 are dimensioned to locate snugly into the receptacle wells 23 so as to effectively displace fluid in each receptacle well whilst allowing gas to vent from the sample wells.

FIGS. 33 to 35 show a sample container 30 consisting of a base 31 with a plurality of container wells 32 extending therefrom. Reactants 33 may be pre-supplied to each container well 32 as will be described below.

In use the elements may be provided separately for a user to supply required reactants to the container wells 32 on site and assemble and use the kit. However, in many applications it may be desirable to provide reactants in each container well at the time of manufacture. As described in relation to the previous embodiment this may consist of a plurality of different antibiotics of different concentrations in each container well or some other desired combination of reactants. The sample receptacle 21 and sample container 30 may then be mated (see FIGS. 36 and 37) during manufacture so that a user has a pre-assembled unit to which a sample fluid may be directly supplied. Where each aperture in each receptacle well is sealed (as described above) then the reactants may be protected from the environment. This arrangement also protects against reactants falling out. The reactants in each container well may also be provided with an inert environment (e.g. inert gas) and/or a growth media etc.

Figure 36:
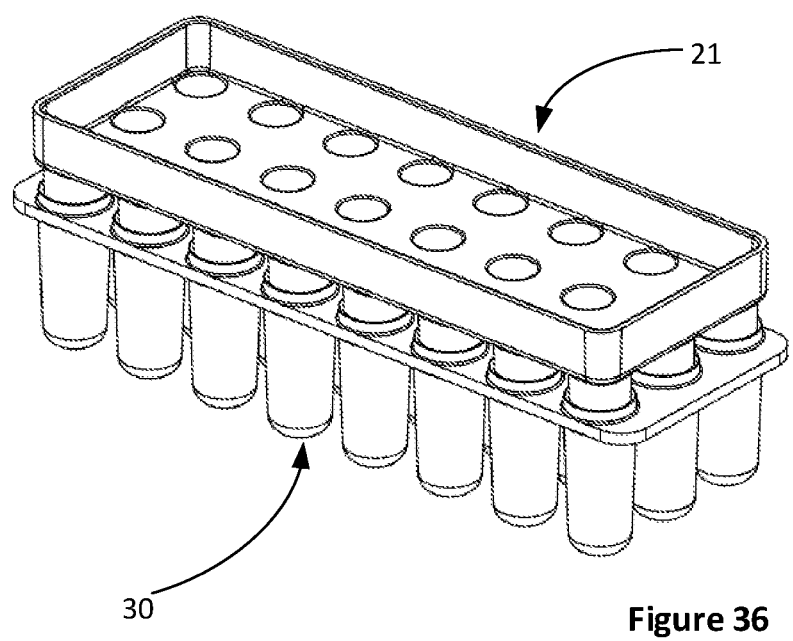
FIG. 36 is a top perspective view of a sample receptacle as shown in FIGS. 25 to 27 mated with a sample container as shown in FIGS. 33 to 35.
Figure 37:
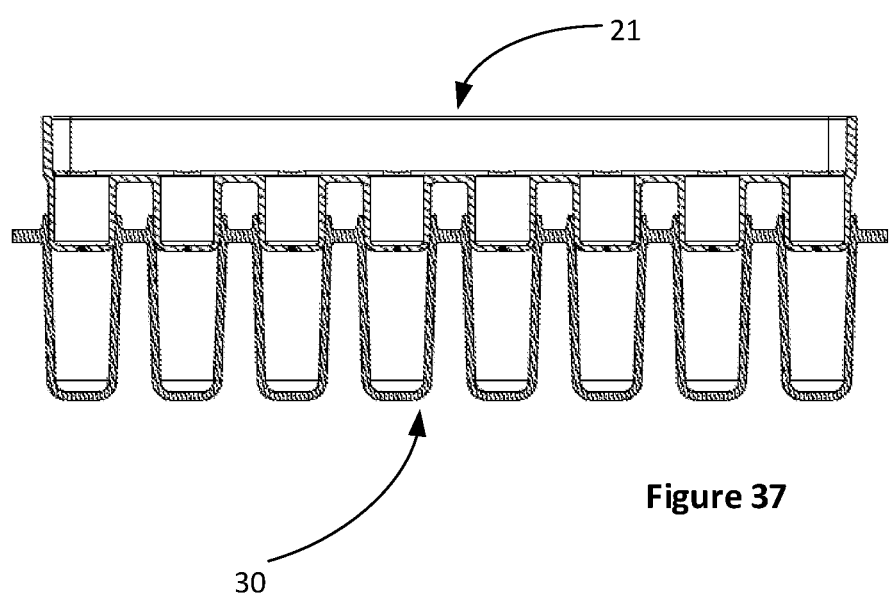
FIG. 37 is a cross-sectional view of the mated sample container and sample receptacle shown in FIG. 36.
Figure 38:
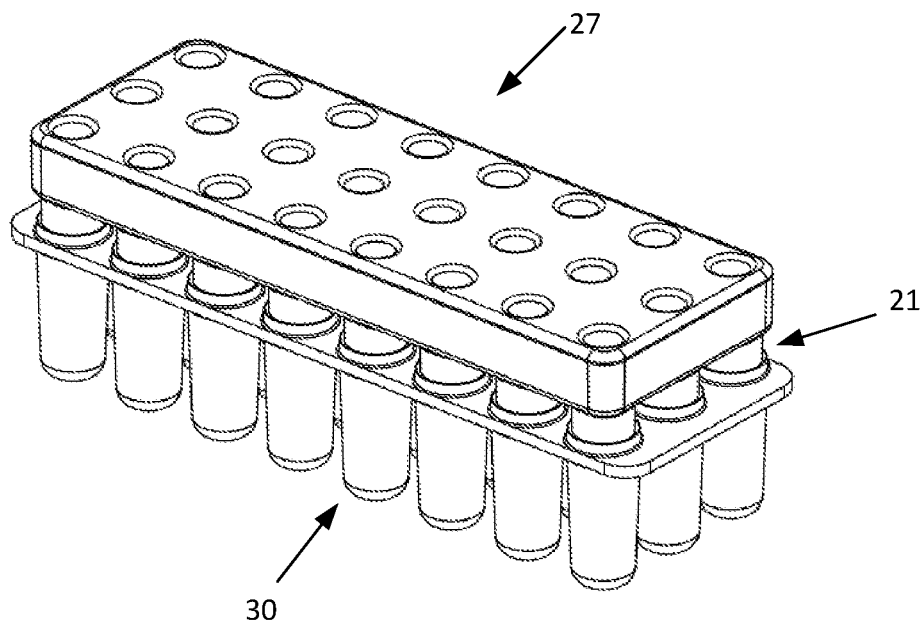
FIG. 38 is a top perspective view showing a plunger assembly as shown in FIGS. 30 to 32 engaged in the cavities of a sample receptacle as shown in FIGS. 25 to 27 mated with a sample container as shown in FIGS. 33 to 35.
Figure 39:
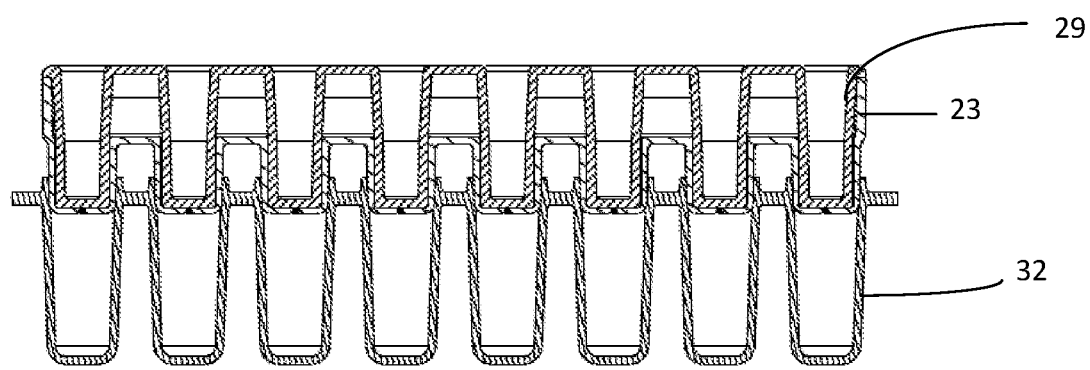
FIG. 39 is a cross-sectional view of the mated plunger assembly, sample container and sample receptacle shown in FIG. 38.

In use reactants 33 are provided in the container wells and the sample receptacle 21 and sample container 30 are mated (see FIGS. 36 and 37). This may either occur during manufacture or on site as discussed above. A sample liquid is then supplied to the sample receptacle 21 to a level above the mouths of the receptacle wells 23 and retained by receptacle wall 22. The mated sample receptacle and sample container may then be inverted to remove excess fluid as in the previous embodiment although this step is not essential in this embodiment. The plunger assembly 27 may then be mated (see FIG. 38) so that the pistons 29 enter the mouths of receptacle wells 23 (see FIG. 39). If there is excess liquid above the mouths of receptacle wells 23 this displaces around pistons 29 until they are engaged with mouths of the receptacle wells 23. In this way a constant volume of liquid is delivered from each well whether there is liquid above the mouth of each well or not. The pistons are then advanced along each receptacle well to eject fluid contained therein into the respective container well below. If a seal is provided over an aperture in the base of a receptacle well the pressure created by advancing each piston will dislodge it to allow fluid to flow through each aperture. Alternatively where a wax or similar seal is provided it may be heated to open each aperture.

This arrangement saves a user from having to dispose of excess liquid from the sample receptacle. It also saves the user having to mate the sample receptacle and sample container where these come pre-assembled. Further this method saves the user having to mix reactants and sample fluid by shaking etc. as the jet of fluid entering each sample well effectively mixes with reactants. This forced approach may also be advantageous for clotted samples.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

Example 1

In this example a receptacle of the form shown in FIGS. 1 to 4 was used to assess the variation in volume per cavity where the sample fluid is full fat homogenised milk. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

| poured off at A8 (user 2) | | | |
| --- | --- | --- | --- |
| | A | B | C |
| R1 | | | |
| 1 | 84 | 91 | 87 |
| 2 | 89 | 96 | 88 |
| 3 | 86 | 91 | 87 |
| 4 | 80 | 96 | 89 |
| 5 | 85 | 96 | 90 |
| 6 | 83 | 95 | 89 |
| 7 | 83 | 86 | 91 |
| 8 | 89 | 86 | 89 |
| | Average | Std | CV |
| ul | 89 | 4 | 4.7% |
| R2 | | | |
| 1 | 83 | 91 | 87 |
| 2 | 88 | 89 | 90 |
| 3 | 84 | 83 | 91 |
| 4 | 85 | 83 | 90 |
| 5 | 83 | 88 | 90 |
| 6 | 82 | 89 | 89 |
| 7 | 80 | 85 | 90 |
| 8 | 39 | 83 | 86 |
| | Average | Std | CV |
| ul | 85 | 10 | 11.9% |
| R3 | | | |
| 1 | 83 | 96 | 87 |
| 2 | 82 | 86 | 86 |
| 3 | 83 | 88 | 88 |
| 4 | 83 | 86 | 88 | poured off at A8 (user 2)

|   | A | B | C |
|---|---|---|---|
| 5 | 83 | 90 | 88 |
| 6 | 84 | 84 | 91 |
| 7 | 84 | 87 | 89 |
| 8 | 56 | 84 | 88 |

|    | Average | Std | CV |
|----|---------|-----|-----|
| ul | 85 | 7 | 8.0% |

R4

|   | A | B | C |
|---|---|---|---|
| 1 | 90 | 87 | 97 |
| 2 | 84 | 83 | 92 |
| 3 | 87 | 93 | 85 |
| 4 | 84 | 91 | 85 |
| 5 | 83 | 89 | 86 |
| 6 | 79 | 87 | 87 |
| 7 | 82 | 87 | 87 |
| 8 | 50 | 82 | 88 |

|    | Average | Std | CV |
|----|---------|-----|-----|
| ul | 85 | 8 | 9.7% |

R5

|   | A | B | C |
|---|---|---|---|
| 1 | 83 | 91 | 89 |
| 2 | 84 | 88 | 85 |
| 3 | 86 | 91 | 87 |
| 4 | 87 | 90 | 88 |
| 5 | 84 | 88 | 89 |
| 6 | 85 | 95 | 90 |
| 7 | 83 | 89 | 90 |
| 8 | 77 | 88 | 91 |

|    | Average | Std | CV |
|----|---------|-----|-----|
| ul | 87 | 4 | 4.1% |

|    | Overall average | Std | CV |
|----|---------|-----|-----|
| ul | 86 | 7 | 8.3% |

Example 2

In this example a receptacle of the form shown in FIGS. 1 to 4 was used to assess the variation in volume per cavity where the sample fluid is full fat homogenised milk. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

poured off at C8 (user 2)

|   | A | B | C |
|---|---|---|---|
| R1 | | | |
| 1 | 88 | 93 | 90 |
| 2 | 90 | 89 | 89 |
| 3 | 77 | 97 | 86 |
| 4 | 88 | 89 | 86 |
| 5 | 91 | 91 | 82 |
| 6 | 89 | 91 | 81 |
| 7 | 91 | 86 | 82 |
| 8 | 30 | 90 | 82 |

|    | Average | Std | CV |
|----|---------|-----|-----|
| ul | 85 | 12 | 14.4% |

R2

|   | A | B | C |
|---|---|---|---|
| 1 | 89 | 92 | 84 |
| 2 | 92 | 92 | 86 |
| 3 | 88 | 86 | 84 |
| 4 | 93 | 89 | 84 |
| 5 | 96 | 89 | 84 |
| 6 | 88 | 89 | 83 |
| 7 | 97 | 88 | 79 |
| 8 | 91 | 91 | 86 |

|    | Average | Std | CV |
|----|---------|-----|-----|
| ul | 88 | 4 | 4.7% |

R3

|   | A | B | C |
|---|---|---|---|
| 1 | 85 | 95 | 87 |
| 2 | 92 | 92 | 85 |
| 3 | 89 | 91 | 85 |
| 4 | 90 | 98 | 83 |
| 5 | 95 | 96 | 90 |
| 6 | 96 | 88 | 72 |
| 7 | 98 | 85 | 77 |
| 8 | 96 | 91 | 89 |

|    | Average | Std | CV |
|----|---------|-----|-----|
| ul | 89 | 6 | 7.0% |

R4

|   | A | B | C |
|---|---|---|---|
| 1 | 86 | 92 | 86 |
| 2 | 91 | 88 | 84 |
| 3 | 89 | 90 | 84 |
| 4 | 91 | 90 | 84 |
| 5 | 92 | 88 | 84 |
| 6 | 93 | 88 | 84 |
| 7 | 94 | 97 | 83 |
| 8 | 96 | 93 | 82 |

|    | Average | Std | CV |
|----|---------|-----|-----|
| ul | 89 | 4 | 4.8% |

R5

|   | A | B | C |
|---|---|---|---|
| 1 | 89 | 91 | 83 |
| 2 | 89 | 93 | 84 |
| 3 | 89 | 95 | 84 |
| 4 | 94 | 96 | 84 |
| 5 | 91 | 98 | 82 |
| 6 | 90 | 97 | 83 |
| 7 | 93 | 90 | 81 |
| 8 | 81 | 91 | 95 |

|    | Average | Std | CV |
|----|---------|-----|-----|
| ul | 89 | 5 | 5.9% |

|    | Overall average | Std | CV |
|----|---------|-----|-----|
| ul | 88 | 7 | 8.3% |

Example 3

In this example a receptacle of the form shown in FIGS. 1 to 4 was used to assess the variation in volume per cavity where the sample fluid is full fat homogenised milk. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

| poured off at A1 (user 2) | | | |
|---|---|---|---|
| | A | B | C |
| R1 | | | |
| 1 | 86 | 85 | 90 |
| 2 | 82 | 89 | 88 |
| 3 | 86 | 87 | 85 |
| 4 | 87 | 85 | 88 |
| 5 | 84 | 89 | 87 |
| 6 | 90 | 96 | 90 |
| 7 | 76 | 97 | 91 |
| 8 | 93 | 95 | 93 |
| | Average | Std | CV |
| ul | 88 | 5 | 5.2% |
| R2 | | | |
| 1 | 80 | 82 | 87 |
| 2 | 77 | 89 | 89 |
| 3 | 82 | 91 | 87 |
| 4 | 81 | 93 | 88 |
| 5 | 83 | 86 | 87 |
| 6 | 87 | 90 | 90 |
| 7 | 79 | 90 | 89 |
| 8 | 53 | 91 | 96 |
| | Average | Std | CV |
| ul | 85 | 8 | 9.5% |
| R3 | | | |
| 1 | 83 | 89 | 89 |
| 2 | 86 | 87 | 91 |
| 3 | 79 | 80 | 88 |
| 4 | 78 | 74 | 92 |
| 5 | 84 | 92 | 88 |
| 6 | 82 | 81 | 82 |
| 7 | 82 | 96 | 91 |
| 8 | 83 | 97 | 98 |
| | Average | Std | CV |
| ul | 86 | 6 | 7.1% |
| R4 | | | |
| 1 | 83 | 86 | 91 |
| 2 | 87 | 89 | 90 |
| 3 | 79 | 59 | 94 |
| 4 | 80 | 81 | 91 |
| 5 | 81 | 68 | 91 |
| 6 | 79 | 87 | 91 |
| 7 | 82 | 86 | 80 |
| 8 | 61 | 95 | 95 |
| | Average | Std | CV |
| ul | 84 | 9 | 11.3% |
| R5 | | | |
| 1 | 88 | 90 | 89 |
| 2 | 88 | 89 | 90 |
| 3 | 80 | 89 | 91 |
| 4 | 82 | 91 | 91 |
| 5 | 92 | 94 | 91 |
| 6 | 83 | 89 | 89 |
| 7 | 87 | 92 | 88 |
| 8 | 36 | 97 | 95 |
| | Average | Std | CV |
| ul | 87 | 11 | 13.0% |
| | Overall average | Std | CV |
| ul | 86 | 8 | 9.8% |

Example 4

In this example a receptacle of the form shown in FIGS. 1 to 4 was used to assess the variation in volume per cavity where the sample fluid is full fat homogenised milk. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

| poured off at C1 (user 2) | | | |
|---|---|---|---|
| | A | B | C |
| R1 | | | |
| 1 | 89 | 87 | 87 |
| 2 | 92 | 87 | 81 |
| 3 | 92 | 89 | 82 |
| 4 | 88 | 95 | 78 |
| 5 | 86 | 93 | 85 |
| 6 | 95 | 94 | 83 |
| 7 | 95 | 97 | 85 |
| 8 | 94 | 98 | 83 |
| | Average | Std | CV |
| ul | 89 | 5 | 6.1% |
| R2 | | | |
| 1 | 88 | 86 | 89 |
| 2 | 89 | 87 | 82 |
| 3 | 89 | 85 | 86 |
| 4 | 84 | 87 | 81 |
| 5 | 93 | 87 | 87 |
| 6 | 95 | 96 | 87 |
| 7 | 94 | 98 | 86 |
| 8 | 93 | 92 | 87 |
| | Average | Std | CV |
| ul | 89 | 4 | 4.8% |
| R3 | | | |
| 1 | 86 | 84 | 90 |
| 2 | 88 | 86 | 81 |
| 3 | 88 | 89 | 79 |
| 4 | 85 | 86 | 82 |
| 5 | 84 | 89 | 81 |
| 6 | 97 | 91 | 83 |

-continued

| poured off at C1 (user 2) | | | |
|---|---|---|---|
| | A | B | C |
| 7 | 89 | 70 | 84 |
| 8 | 88 | 98 | 84 |
| | Average | Std | CV |
| ul | 86 | 6 | 6.5% |
| R4 | | | |
| 1 | 85 | 86 | 87 |
| 2 | 87 | 87 | 77 |
| 3 | 86 | 84 | 78 |
| 4 | 87 | 91 | 80 |
| 5 | 88 | 91 | 80 |
| 6 | 84 | 61 | 78 |
| 7 | 85 | 92 | 82 |
| 8 | 92 | 89 | 81 |
| | Average | Std | CV |
| ul | 84 | 6 | 7.7% |
| R5 | | | |
| 1 | 86 | 83 | 79 |
| 2 | 88 | 86 | 79 |
| 3 | 86 | 86 | 76 |
| 4 | 90 | 84 | 81 |
| 5 | 85 | 88 | 78 |
| 6 | 94 | 87 | 83 |
| 7 | 84 | 93 | 80 |
| 8 | 93 | 92 | 80 |
| | Average | Std | CV |
| ul | 85 | 5 | 5.8% |
| | Overall | | |
| | average | Std | CV |
| ul | 87 | 6 | 6.6% |

Example 5

In this example a receptacle of the form shown in FIGS. 1 to 4 was used to assess the variation in volume per cavity where the sample fluid is full fat homogenised milk. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

| poured off at A1 (user 1) | | | |
|---|---|---|---|
| | A | B | C |
| R1 | | | |
| 1 | 75 | 91 | 84 |
| 2 | 59 | 91 | 80 |
| 3 | 80 | 90 | 81 |
| 4 | 80 | 94 | 87 |
| 5 | 81 | 93 | 86 |
| 6 | 78 | 86 | 88 |
| 7 | 77 | 83 | 86 |
| 8 | 85 | 81 | 87 |
| | Average | Std | CV |
| ul | 83 | 7 | 8.5% |
| R2 | | | |
| 1 | 80 | 89 | 87 |
| 2 | 77 | 89 | 87 |
| 3 | 79 | 94 | 86 |

-continued

| poured off at A1 (user 1) | | | |
|---|---|---|---|
| | A | B | C |
| 4 | 80 | 86 | 96 |
| 5 | 78 | 84 | 90 |
| 6 | 75 | 93 | 91 |
| 7 | 79 | 85 | 87 |
| 8 | 84 | 83 | 83 |
| | Average | Std | CV |
| ul | 85 | 5 | 6.4% |
| R3 | | | |
| 1 | 84 | 87 | 91 |
| 2 | 81 | 92 | 89 |
| 3 | 82 | 88 | 91 |
| 4 | 75 | 86 | 89 |
| 5 | 76 | 85 | 84 |
| 6 | 81 | 83 | 52 |
| 7 | 80 | 80 | 86 |
| 8 | 85 | 80 | 81 |
| | Average | Std | CV |
| ul | 83 | 8 | 9.4% |
| R4 | | | |
| 1 | 82 | 88 | 84 |
| 2 | 79 | 90 | 91 |
| 3 | 81 | 82 | 85 |
| 4 | 77 | 86 | 54 |
| 5 | 72 | 88 | 85 |
| 6 | 80 | 84 | 87 |
| 7 | 77 | 86 | 83 |
| 8 | 82 | 78 | 82 |
| | Average | Std | CV |
| ul | 82 | 7 | 8.9% |
| R5 | | | |
| 1 | 79 | 84 | 79 |
| 2 | 77 | 84 | 92 |
| 3 | 79 | 84 | 59 |
| 4 | 79 | 81 | 82 |
| 5 | 82 | 77 | 82 |
| 6 | 75 | 88 | 89 |
| 7 | 76 | 80 | 85 |
| 8 | 87 | 84 | 83 |
| | Average | Std | CV |
| ul | 81 | 6 | 7.6% |
| | Overall | | |
| | average | Std | CV |
| ul | 83 | 7 | 8.4% |

Example 6

In this example a receptacle of the form shown in FIGS. 1 to 4 was used to assess the variation in volume per cavity where the sample fluid is full fat homogenised milk. The receptacle has 3 rows A to C and eight columns 1 to 8. The cavities have no vent hole. The five tests R1 to R5 show the volumes in each cavity in ul, the average volume in each cavity, the standard deviation (Std) and the coefficient of variation (CV) and at the end the Std and CV for all tests.

| Sample receptacle with closed venting holes | | | |
|---|---|---|---|
| | A | B | C |
| R1 | | | |
| 1 | 14 | 12 | 85 |
| 2 | 22 | 87 | 84 |
| 3 | 3 | 92 | 7 |
| 4 | 3 | 91 | 7 |
| 5 | 14 | 96 | 87 |
| 6 | 2 | 90 | 87 |
| 7 | 3 | 3 | 88 |
| 8 | 9 | 3 | 92 |
| | Average | Std | CV |
| ul | 45 | 41 | 90.4% |
| R2 | | | |
| 1 | 6 | 4 | 13 |
| 2 | 1 | 4 | 17 |
| 3 | 5 | 7 | 12 |
| 4 | 15 | 10 | 13 |
| 5 | 9 | 1 | 9 |
| 6 | 6 | 4 | 27 |
| 7 | 1 | 7 | 87 |
| 8 | 7 | 99 | 58 |
| | Average | Std | CV |
| ul | 18 | 25 | 145.0% |
| R3 | | | |
| 1 | 15 | 84 | 9 |
| 2 | 0 | 79 | 9 |
| 3 | 17 | 6 | 18 |
| 4 | 23 | 72 | 22 |
| 5 | 27 | 88 | 8 |
| 6 | 88 | 88 | 9 |
| 7 | 87 | 89 | 8 |
| 8 | 88 | 93 | 14 |
| | Average | Std | CV |
| ul | 43 | 36 | 83.7% |
| R4 | | | |
| 1 | 81 | 6 | 18 |
| 2 | 10 | 4 | 6 |
| 3 | 16 | 50 | 1 |
| 4 | 92 | 95 | 1 |
| 5 | 91 | 96 | 33 |
| 6 | 91 | 1 | 23 |
| 7 | 7 | 7 | 2 |
| 8 | 80 | 95 | 90 |
| | Average | Std | CV |
| ul | 42 | 39 | 94.6% |
| R5 | | | |
| 1 | 85 | 84 | 84 |
| 2 | 76 | 87 | 35 |
| 3 | 76 | 86 | 12 |
| 4 | 4 | 1 | 46 |
| 5 | 4 | 4 | 52 |
| 6 | 51 | 6 | 92 |

-continued

| Sample receptacle with closed venting holes | | | |
|---|---|---|---|
| | A | B | C |
| 7 | 8 | 86 | 91 |
| 8 | 2 | 96 | 91 |
| | Average | Std | CV |
| ul | 52 | 37 | 70.0% |
| | Overall average | Std | CV |
| ul | 40 | 38 | 95.0% |

Example 7

In this example a receptacle of the form shown in FIGS. 1 to 4 was used to assess the variation in volume per cavity where the sample fluid is full fat homogenised milk. The receptacle has 3 rows A to C and eight columns 1 to 8. A cylindrical vent hole having a diameter of 0.2 mm is provided in the base of each cavity. The liquid samples in each cavity were delivered into respective wells of a sample container. The five tests C1 to C5 show the volumes in each well in ul, the average volume in each well, the standard deviation (Std) and the coefficient of variation (CV) and at the end the Std and CV for all tests.

| Sample Container | | | |
|---|---|---|---|
| | A | B | C |
| C1 | | | |
| 1 | 72 | 87 | 75 |
| 2 | 78 | 90 | 79 |
| 3 | 65 | 82 | 74 |
| 4 | 63 | 80 | 82 |
| 5 | 78 | 89 | 85 |
| 6 | 74 | 91 | 76 |
| 7 | 67 | 84 | 76 |
| 8 | 74 | 78 | 77 |
| | Average | Std | CV |
| ul | 78 | 7 | 9.2% |
| C2 | | | |
| 1 | 76 | 76 | 77 |
| 2 | 62 | 78 | 66 |
| 3 | 70 | 73 | 76 |
| 4 | 69 | 76 | 77 |
| 5 | 77 | 85 | 78 |
| 6 | 73 | 79 | 68 |
| 7 | 81 | 88 | 73 |
| 8 | 72 | 86 | 85 |
| | Average | Std | CV |
| ul | 76 | 6 | 8.2% |
| C3 | | | |
| 1 | 87 | 73 | 89 |
| 2 | 82 | 81 | 78 |
| 3 | 77 | 84 | 75 |
| 4 | 82 | 78 | 82 |
| 5 | 76 | 84 | 84 |
| 6 | 83 | 77 | 83 |

-continued

| Sample Container | | | |
|---|---|---|---|
| | A | B | C |
| 7 | 75 | 82 | 78 |
| 8 | 81 | 83 | 71 |

| | Average | Std | CV |
|---|---|---|---|
| ul | 80 | 4 | 5.4% |

C4

| | A | B | C |
|---|---|---|---|
| 1 | 70 | 73 | 62 |
| 2 | 78 | 84 | 63 |
| 3 | 68 | 79 | 68 |
| 4 | 78 | 73 | 73 |
| 5 | 76 | 84 | 71 |
| 6 | 85 | 65 | 75 |
| 7 | 72 | 78 | 67 |
| 8 | 78 | 96 | 71 |

| | Average | Std | CV |
|---|---|---|---|
| ul | 74 | 8 | 10.3% |

C5

| | A | B | C |
|---|---|---|---|
| 1 | 65 | 73 | 74 |
| 2 | 75 | 84 | 69 |
| 3 | 74 | 85 | 73 |
| 4 | 71 | 88 | 84 |
| 5 | 84 | 83 | 88 |
| 6 | 83 | 82 | 82 |
| 7 | 77 | 86 | 71 |
| 8 | 73 | 80 | 83 |

| | Average | Std | CV |
|---|---|---|---|
| ul | 79 | 6 | 8.2% |

| | Overall average | Std | CV |
|---|---|---|---|
| ul | 77 | 7 | 8.8% |

Example 8

In this example a receptacle of the form shown in FIGS. 1 to 4 was used to assess the variation in volume per cavity where the sample fluid is 10% whole milk powder liquid (reconstituted). The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

| Sample receptacle with venting holes | | | |
|---|---|---|---|
| | A | B | C |
| R1 | | | |
| 1 | 76 | 85 | 89 |
| 2 | 83 | 88 | 90 |
| 3 | 86 | 91 | 90 |
| 4 | 86 | 89 | 94 |
| 5 | 87 | 93 | 90 |
| 6 | 89 | 91 | 93 |

-continued

| Sample receptacle with venting holes | | | |
|---|---|---|---|
| | A | B | C |
| 7 | 92 | 94 | 91 |
| 8 | 89 | 96 | 91 |

| | Average | Std | CV |
|---|---|---|---|
| ul | 89 | 4 | 4.6% |

R2

| | A | B | C |
|---|---|---|---|
| 1 | 78 | 85 | 87 |
| 2 | 83 | 87 | 92 |
| 3 | 88 | 89 | 88 |
| 4 | 85 | 86 | 87 |
| 5 | 86 | 81 | 93 |
| 6 | 88 | 90 | 87 |
| 7 | 88 | 90 | 82 |
| 8 | 88 | 95 | 86 |

| | Average | Std | CV |
|---|---|---|---|
| ul | 87 | 4 | 4.2% |

R3

| | A | B | C |
|---|---|---|---|
| 1 | 78 | 86 | 87 |
| 2 | 86 | 87 | 91 |
| 3 | 85 | 86 | 86 |
| 4 | 83 | 90 | 89 |
| 5 | 86 | 95 | 92 |
| 6 | 81 | 93 | 86 |
| 7 | 84 | 95 | 94 |
| 8 | 86 | 96 | 90 |

| | Average | Std | CV |
|---|---|---|---|
| ul | 88 | 5 | 5.1% |

R4

| | A | B | C |
|---|---|---|---|
| 1 | 81 | 85 | 89 |
| 2 | 78 | 88 | 90 |
| 3 | 84 | 91 | 87 |
| 4 | 86 | 90 | 90 |
| 5 | 85 | 88 | 90 |
| 6 | 85 | 96 | 95 |
| 7 | 84 | 94 | 93 |
| 8 | 86 | 90 | 91 |

| | Average | Std | CV |
|---|---|---|---|
| ul | 88 | 4 | 4.8% |

R5

| | A | B | C |
|---|---|---|---|
| 1 | 80 | 84 | 89 |
| 2 | 81 | 88 | 87 |
| 3 | 84 | 85 | 89 |
| 4 | 84 | 87 | 89 |
| 5 | 85 | 95 | 89 |
| 6 | 85 | 86 | 94 |
| 7 | 88 | 48 | 93 |
| 8 | 84 | 92 | 89 |

| | Average | Std | CV |
|---|---|---|---|
| ul | 86 | 9 | 10.1% |

| | Overall average | Std | CV |
|---|---|---|---|
| ul | 88 | 5 | 6.3% |

Example 9

In this example a receptacle of the form shown in FIGS. 1 to 4 was used to assess the variation in volume per cavity where the sample fluid is 10% whole milk powder liquid (reconstituted). The receptacle has 3 rows A to C and eight columns 1 to 8. A cylindrical vent hole having a diameter of 0.2 mm is provided in the base of each cavity. The liquid samples in each cavity were delivered into respective wells of a sample container. The five tests C1 to C5 show the volumes in each well in ul, the average volume in each cavity, the standard deviation (Std) and the coefficient of variation (CV) and at the end the Std and CV for all tests.

| | Sample Container | | |
|---|---|---|---|
| | A | B | C |
| C1 | | | |
| 1 | 80 | 70 | 73 |
| 2 | 76 | 79 | 75 |
| 3 | 76 | 87 | 75 |
| 4 | 80 | 78 | 72 |
| 5 | 79 | 80 | 74 |
| 6 | 81 | 88 | 67 |
| 7 | 81 | 95 | 87 |
| 8 | 80 | 90 | 78 |
| | Average | Std | CV |
| ul | 79 | 6 | 8.1% |
| C2 | | | |
| 1 | 76 | 68 | 71 |
| 2 | 78 | 78 | 76 |
| 3 | 74 | 79 | 74 |
| 4 | 82 | 79 | 75 |
| 5 | 82 | 78 | 73 |
| 6 | 83 | 83 | 71 |
| 7 | 81 | 90 | 71 |
| 8 | 79 | 87 | 78 |
| | Average | Std | CV |
| ul | 78 | 5 | 6.6% |
| C3 | | | |
| 1 | 67 | 74 | 70 |
| 2 | 74 | 74 | 77 |
| 3 | 77 | 80 | 71 |
| 4 | 73 | 70 | 76 |
| 5 | 79 | 73 | 74 |
| 6 | 73 | 81 | 71 |
| 7 | 79 | 88 | 78 |
| 8 | 71 | 85 | 79 |
| | Average | Std | CV |
| ul | 76 | 5 | 6.4% |
| C4 | | | |
| 1 | 76 | 71 | 66 |
| 2 | 80 | 74 | 65 |
| 3 | 81 | 74 | 69 |
| 4 | 82 | 70 | 74 |
| 5 | 84 | 83 | 73 |
| 6 | 83 | 77 | 75 |
| 7 | 71 | 87 | 66 |
| 8 | 67 | 85 | 74 |
| | Average | Std | CV |
| ul | 75 | 6 | 8.5% |

-continued

| | Sample Container | | |
|---|---|---|---|
| | A | B | C |
| C5 | | | |
| 1 | 76 | 73 | 58 |
| 2 | 72 | 67 | 63 |
| 3 | 74 | 68 | 76 |
| 4 | 73 | 69 | 69 |
| 5 | 85 | 77 | 71 |
| 6 | 73 | 72 | 69 |
| 7 | 69 | 82 | 70 |
| 8 | 75 | 86 | 69 |
| | Average | Std | CV |
| ul | 72 | 6 | 8.5% |
| | Overall average | Std | CV |
| ul | 76 | 6 | 8.3% |

Example 10

In this example a receptacle of the form shown in FIGS. 1 to 4 was used to assess the variation in volume per cavity where the sample fluid is 10% whole milk powder liquid (reconstituted). The receptacle has 3 rows A to C and eight columns 1 to 8. No vent hole is provided in the cavities in this example. The five tests R1 to R5 show the volumes in each cavity in ul, the average volume in each cavity, the standard deviation (Std) and the coefficient of variation (CV) and at the end the Std and CV for all tests.

| | Sample receptacle with closed venting holes | | |
|---|---|---|---|
| | A | B | C |
| R1 | | | |
| 1 | 7 | 0 | 13 |
| 2 | 4 | 2 | 15 |
| 3 | 4 | 0 | 12 |
| 4 | 4 | 12 | 40 |
| 5 | 7 | 95 | 81 |
| 6 | 1 | 100 | 9 |
| 7 | 1 | 99 | 40 |
| 8 | 93 | 7 | 96 |
| | Average | Std | CV |
| ul | 31 | 38 | 122.6% |
| R2 | | | |
| 1 | 0 | 4 | 11 |
| 2 | 8 | 0 | 14 |
| 3 | 21 | 3 | 21 |
| 4 | 36 | 94 | 99 |
| 5 | 1 | 101 | 47 |
| 6 | 33 | 77 | 19 |
| 7 | 2 | 96 | 95 |
| 8 | 5 | 92 | 8 |
| | Average | Std | CV |
| ul | 37 | 38 | 103.4% |
| R3 | | | |
| 1 | 9 | 4 | 13 |
| 2 | 5 | 3 | 11 |

-continued

Sample receptacle with closed venting holes

|  | A | B | C |
|---|---|---|---|
| 3 | 12 | 55 | 16 |
| 4 | 57 | 95 | 6 |
| 5 | 9 | 97 | 3 |
| 6 | 8 | 101 | 6 |
| 7 | 0 | 99 | 8 |
| 8 | 0 | 94 | 8 |

|  | Average | Std | CV |
|---|---|---|---|
| ul | 30 | 37 | 124.1% |

R4

|  | A | B | C |
|---|---|---|---|
| 1 | 2 | 0 | 3 |
| 2 | 5 | 94 | 7 |
| 3 | 91 | 95 | 27 |
| 4 | 90 | 99 | 8 |
| 5 | 93 | 94 | 4 |
| 6 | 91 | 4 | 10 |
| 7 | 93 | 92 | 94 |
| 8 | 5 | 4 | 9 |

|  | Average | Std | CV |
|---|---|---|---|
| ul | 46 | 43 | 93.5% |

R5

|  | A | B | C |
|---|---|---|---|
| 1 | 12 | 0 | 10 |
| 2 | 0 | 100 | 7 |
| 3 | 4 | 11 | 9 |
| 4 | 2 | 93 | 5 |
| 5 | 20 | 12 | 13 |
| 6 | 93 | 41 | 8 |
| 7 | 92 | 102 | 7 |
| 8 | 0 | 5 | 10 |

|  | Average | Std | CV |
|---|---|---|---|
| ul | 27 | 36 | 132.3% |

|  | Overall average | Std | CV |
|---|---|---|---|
| ul | 34 | 39 | 114.4% |

Example 11

In this example a receptacle of the form shown in FIGS. 1 to 4 was used to assess the variation in volume per cavity where the sample fluid is sheep blood. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

Sample receptacle with venting holes

|  | A | B | C |
|---|---|---|---|
| R1 |  |  |  |
| 1 | 83 | 90 | 91 |
| 2 | 85 | 91 | 90 |
| 3 | 92 | 97 | 92 |
| 4 | 86 | 29 | 85 |
| 5 | 86 | 91 | 93 |
| 6 | 86 | 92 | 93 |

-continued

Sample receptacle with venting holes

|  | A | B | C |
|---|---|---|---|
| 7 | 90 | 94 | 98 |
| 8 | 89 | 93 | 92 |

|  | Average | Std | CV |
|---|---|---|---|
| ul | 88 | 13 | 14.6% |

R2

|  | A | B | C |
|---|---|---|---|
| 1 | 82 | 90 | 88 |
| 2 | 79 | 88 | 88 |
| 3 | 84 | 95 | 83 |
| 4 | 86 | 95 | 90 |
| 5 | 81 | 88 | 94 |
| 6 | 83 | 88 | 93 |
| 7 | 84 | 98 | 85 |
| 8 | 89 | 102 | 90 |

|  | Average | Std | CV |
|---|---|---|---|
| ul | 88 | 5 | 6.2% |

R3

|  | A | B | C |
|---|---|---|---|
| 1 | 85 | 92 | 89 |
| 2 | 83 | 90 | 87 |
| 3 | 87 | 91 | 90 |
| 4 | 83 | 94 | 89 |
| 5 | 80 | 88 | 85 |
| 6 | 85 | 89 | 85 |
| 7 | 85 | 87 | 87 |
| 8 | 85 | 96 | 88 |

|  | Average | Std | CV |
|---|---|---|---|
| ul | 88 | 4 | 4.1% |

R4

|  | A | B | C |
|---|---|---|---|
| 1 | 80 | 87 | 89 |
| 2 | 82 | 90 | 89 |
| 3 | 81 | 92 | 89 |
| 4 | 83 | 87 | 90 |
| 5 | 82 | 92 | 89 |
| 6 | 78 | 91 | 87 |
| 7 | 88 | 88 | 88 |
| 8 | 82 | 93 | 92 |

|  | Average | Std | CV |
|---|---|---|---|
| ul | 87 | 4 | 4.8% |

R5

|  | A | B | C |
|---|---|---|---|
| 1 | 79 | 85 | 84 |
| 2 | 85 | 85 | 88 |
| 3 | 83 | 90 | 80 |
| 4 | 85 | 87 | 88 |
| 5 | 80 | 91 | 91 |
| 6 | 81 | 93 | 84 |
| 7 | 86 | 46 | 87 |
| 8 | 83 | 88 | 88 |

|  | Average | Std | CV |
|---|---|---|---|
| ul | 84 | 9 | 10.4% |

|  | Overall average | Std | CV |
|---|---|---|---|
| ul | 87 | 8 | 9.1% |

Example 12

In this example a receptacle of the form shown in FIGS. 1 to 4 was used to assess the variation in volume per cavity where the sample fluid is sheep blood. The receptacle has 3 rows A to C and eight columns 1 to 8. No vent holes were provided in the cavities. The liquid samples in each cavity were delivered into respective wells of a sample container. The five tests C1 to C5 show the volumes in each cavity in ul, the average volume in each well, the standard deviation (Std) and the coefficient of variation (CV) and at the end the Std and CV for all tests.

| Sample receptacle with closed vents | | | |
|---|---|---|---|
| | A | B | C |
| R1 | | | |
| 1 | 84 | 87 | 89 |
| 2 | 81 | 92 | 88 |
| 3 | 25 | 92 | 89 |
| 4 | 27 | 87 | 91 |
| 5 | 29 | 86 | 91 |
| 6 | 10 | 90 | 13 |
| 7 | 13 | 88 | 13 |
| 8 | 11 | 98 | 100 |
| | Average | Std | CV |
| ul | 66 | 34 | 52.4% |
| R2 | | | |
| 1 | 78 | 85 | 7 |
| 2 | 85 | 89 | 9 |
| 3 | 83 | 90 | 7 |
| 4 | 81 | 84 | 14 |
| 5 | 29 | 88 | 87 |
| 6 | 33 | 88 | 7 |
| 7 | 33 | 89 | 20 |
| 8 | 6 | 97 | 96 |
| | Average | Std | CV |
| ul | 58 | 36 | 61.9% |
| R3 | | | |
| 1 | 81 | 90 | 12 |
| 2 | 83 | 85 | 9 |
| 3 | 85 | 91 | 9 |
| 4 | 2 | 87 | 89 |
| 5 | 21 | 91 | 83 |
| 6 | 16 | 87 | 93 |
| 7 | 14 | 46 | 51 |
| 8 | 11 | 93 | 68 |
| | Average | Std | CV |
| ul | 58 | 35 | 59.9% |
| R4 | | | |
| 1 | 15 | 81 | 11 |
| 2 | 3 | 88 | 81 |
| 3 | 3 | 86 | 86 |
| 4 | 2 | 2 | 87 |
| 5 | 3 | 95 | 86 |
| 6 | 6 | 93 | 86 |
| 7 | 10 | 92 | 87 |
| 8 | 6 | 88 | 83 |
| | Average | Std | CV |
| ul | 53 | 40 | 75.2% |
| R5 | | | |
| 1 | 87 | 82 | 87 |
| 2 | 71 | 86 | 83 |
| 3 | 80 | 88 | 14 |
| 4 | 78 | 2 | 8 |
| 5 | 81 | 88 | 12 |
| 6 | 77 | 88 | 12 |
| 7 | 84 | 88 | 95 |
| 8 | 88 | 84 | 9 |
| | Average | Std | CV |
| ul | 66 | 33 | 49.9% |
| Overall average | Std | CV | |
| ul | 60 | 36 | 59.9% |

Example 13

In this example a receptacle of the form shown in FIGS. 1 to 4 was used to assess the variation in volume per cavity where the sample fluid is urine. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

| Sample receptacle with venting holes | | | |
|---|---|---|---|
| | A | B | C |
| R1 | | | |
| 1 | 81 | 87 | 90 |
| 2 | 82 | 91 | 92 |
| 3 | 87 | 89 | 91 |
| 4 | 87 | 84 | 90 |
| 5 | 87 | 93 | 89 |
| 6 | 87 | 97 | 90 |
| 7 | 87 | 97 | 91 |
| 8 | 87 | 95 | 91 |
| | Average | Std | CV |
| ul | 89 | 4 | 4.4% |
| R2 | | | |
| 1 | 85 | 88 | 84 |
| 2 | 84 | 90 | 90 |
| 3 | 84 | 91 | 93 |
| 4 | 85 | 89 | 92 |
| 5 | 87 | 93 | 89 |
| 6 | 86 | 95 | 89 |

| Sample receptacle with venting holes | | | |
|---|---|---|---|
| | A | B | C |
| 7 | 86 | 90 | 94 |
| 8 | 87 | 87 | 91 |
| | Average | Std | CV |
| ul | 89 | 3 | 3.6% |
| R3 | | | |
| 1 | 84 | 81 | 92 |
| 2 | 84 | 87 | 89 |
| 3 | 82 | 92 | 91 |
| 4 | 89 | 90 | 91 |
| 5 | 87 | 90 | 90 |
| 6 | 88 | 88 | 89 |
| 7 | 87 | 94 | 78 |
| 8 | 91 | 91 | 89 |
| ul | Average | Std | CV |
| | 88 | 4 | 4.3% |
| R4 | | | |
| 1 | 80 | 87 | 87 |
| 2 | 85 | 89 | 93 |
| 3 | 87 | 89 | 91 |
| 4 | 85 | 88 | 89 |
| 5 | 88 | 92 | 91 |
| 6 | 88 | 93 | 86 |
| 7 | 85 | 96 | 90 |
| 8 | 89 | 91 | 94 |
| | Average | Std | CV |
| ul | 89 | 3 | 3.8% |
| R5 | | | |
| 1 | 79 | 86 | 83 |
| 2 | 83 | 85 | 90 |
| 3 | 83 | 88 | 88 |
| 4 | 80 | 88 | 90 |
| 5 | 87 | 85 | 89 |
| 6 | 86 | 85 | 90 |
| 7 | 82 | 85 | 91 |
| 8 | 85 | 92 | 91 |
| | Average | Std | CV |
| ul | 86 | 3 | 4.0% |
| | Overall average | Std | CV |
| ul | 88 | 4 | 4.2% |

Example 14

In this example a receptacle of the form shown in FIGS. 1 to 4 was used to assess the variation in volume per cavity where the sample fluid is urine. The receptacle has 3 rows A to C and eight columns 1 to 8. A cylindrical vent hole having a diameter of 0.2 mm is provided in the base of each cavity. The liquid samples in each cavity were delivered into respective wells of a sample container. The five tests C1 to C5 show the volumes in each well in ul, the average volume in each cavity, the standard deviation (Std) and the coefficient of variation (CV) and at the end the Std and CV for all tests.

| Sample Container | | | |
|---|---|---|---|
| | A | B | C |
| C1 | | | |
| 1 | 75 | 71 | 77 |
| 2 | 64 | 69 | 57 |
| 3 | 67 | 73 | 53 |
| 4 | 64 | 78 | 73 |
| 5 | 76 | 64 | 77 |
| 6 | 61 | 70 | 89 |
| 7 | 81 | 76 | 78 |
| 8 | 64 | 70 | 57 |
| | Average | Std | CV |
| ul | 70 | 8 | 11.9% |
| C2 | | | |
| 1 | 87 | 73 | 73 |
| 2 | 64 | 86 | 72 |
| 3 | 58 | 71 | 80 |
| 4 | 78 | 70 | 78 |
| 5 | 86 | 84 | 82 |
| 6 | 84 | 87 | 69 |
| 7 | 71 | 88 | 84 |
| 8 | 71 | 74 | 74 |
| | Average | Std | CV |
| ul | 77 | 8 | 10.3% |
| C3 | | | |
| 1 | 80 | 79 | 67 |
| 2 | 94 | 80 | 72 |
| 3 | 74 | 79 | 72 |
| 4 | 82 | 84 | 82 |
| 5 | 70 | 80 | 74 |
| 6 | 75 | 78 | 78 |
| 7 | 72 | 62 | 83 |
| 8 | 67 | 79 | 88 |
| | Average | Std | CV |
| ul | 77 | 7 | 9.0% |
| C4 | | | |
| 1 | 78 | 82 | 88 |
| 2 | 80 | 84 | 92 |
| 3 | 85 | 90 | 88 |
| 4 | 85 | 86 | 91 |
| 5 | 85 | 88 | 90 |
| 6 | 85 | 90 | 97 |
| 7 | 88 | 90 | 88 |
| 8 | 88 | 94 | 91 |
| | Average | Std | CV |
| ul | 88 | 4 | 4.8% |
| C5 | | | |
| 1 | 63 | 77 | 77 |
| 2 | 69 | 71 | 76 |
| 3 | 73 | 68 | 74 |
| 4 | 67 | 69 | 73 |
| 5 | 76 | 83 | 71 |
| 6 | 68 | 73 | 67 |

-continued

| Sample Container | | | |
|---|---|---|---|
| | A | B | C |
| 7 | 75 | 71 | 65 |
| 8 | 76 | 70 | 81 |
| | Average | Std | CV |
| ul | 72 | 5 | 6.6% |
| | Overall average | Std | CV |
| ul | 77 | 9 | 11.7% |

Example 15

In this example a receptacle of the form shown in FIGS. 1 to 4 was used to assess the variation in volume per cavity where the sample fluid is urine. The receptacle has 3 rows A to C and eight columns 1 to 8. The cavities have no vent hole. The five tests R1 to R5 show the volumes in each cavity in ul, the average volume in each cavity, the standard deviation (Std) and the coefficient of variation (CV) and at the end the Std and CV for all tests.

| Sample receptacle with closed venting holes | | | |
|---|---|---|---|
| | A | B | C |
| R1 | | | |
| 1 | 0 | 0 | 9 |
| 2 | 2 | 0 | 13 |
| 3 | 2 | 1 | 1 |
| 4 | 4 | 7 | 4 |
| 5 | 3 | 3 | 2 |
| 6 | 6 | 0 | 8 |
| 7 | 4 | 91 | 35 |
| 8 | 1 | 0 | 0 |
| | Average | Std | CV |
| ul | 8 | 19 | 228.9% |
| R2 | | | |
| 1 | 6 | 0 | 10 |
| 2 | 3 | 0 | 8 |
| 3 | 9 | 1 | 5 |
| 4 | 2 | 0 | 7 |
| 5 | 3 | 97 | 95 |
| 6 | 2 | 2 | 2 |
| 7 | 0 | 96 | 3 |
| 8 | 3 | 96 | 3 |
| | Average | Std | CV |
| ul | 19 | 35 | 183.3% |
| R3 | | | |
| 1 | 1 | 0 | 3 |
| 2 | 2 | 0 | 5 |
| 3 | 8 | 1 | 8 |
| 4 | 3 | 0 | 6 |
| 5 | 2 | 92 | 2 |
| 6 | 94 | 94 | 5 |

-continued

| Sample receptacle with closed venting holes | | | |
|---|---|---|---|
| | A | B | C |
| 7 | 0 | 95 | 95 |
| 8 | 5 | 95 | 95 |
| | Average | Std | CV |
| ul | 30 | 42 | 140.3% |
| R4 | | | |
| 1 | 0 | 0 | 2 |
| 2 | 2 | 1 | 0 |
| 3 | 90 | 0 | 0 |
| 4 | 5 | 99 | 38 |
| 5 | 3 | 0 | 12 |
| 6 | 0 | 97 | 7 |
| 7 | 0 | 70 | 0 |
| 8 | 0 | 42 | 94 |
| | Average | Std | CV |
| ul | 23 | 36 | 154.3% |
| R5 | | | |
| 1 | 0 | 0 | 0 |
| 2 | 1 | 0 | 6 |
| 3 | 1 | 93 | 2 |
| 4 | 0 | 95 | 2 |
| 5 | 16 | 94 | 1 |
| 6 | 3 | 93 | 2 |
| 7 | 2 | 1 | 58 |
| 8 | 0 | 3 | 8 |
| | Average | Std | CV |
| ul | 20 | 35 | 174.3% |
| | Overall average | Std | CV |
| ul | 20 | 35 | 173.6% |

Example 16

In this example a receptacle of the form shown in FIGS. 1 to 4 was used to assess the variation in volume per cavity where the sample fluid is mastitis milk. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

| Sample receptacle with venting holes | | | |
|---|---|---|---|
| | A | B | C |
| R1 | | | |
| 1 | 62 | 63 | 61 |
| 2 | 61 | 64 | 55 |
| 3 | 55 | 64 | 59 |
| 4 | 58 | 62 | 51 |
| 5 | 56 | 66 | 53 |
| 6 | 57 | 58 | 45 |

Sample receptacle with venting holes

| | A | B | C |
|---|---|---|---|
| 7 | 62 | 61 | 47 |
| 8 | 74 | 73 | 53 |

| | Average | Std | CV |
|---|---|---|---|
| ul | 59 | 5 | 9.2% |

R2

| | A | B | C |
|---|---|---|---|
| 1 | 63 | 69 | 46 |
| 2 | 66 | 73 | 57 |
| 3 | 52 | 73 | 54 |
| 4 | 65 | 68 | 63 |
| 5 | 63 | 65 | 70 |
| 6 | 58 | 67 | 62 |
| 7 | 53 | 64 | 60 |
| 8 | 66 | 59 | 62 |

| | Average | Std | CV |
|---|---|---|---|
| ul | 62 | 7 | 11.1% |

| | Overall average | Std | CV |
|---|---|---|---|
| ul | 61 | 7 | 10.8% |

Example 17

In this example a receptacle of the form shown in FIGS. 1 to 4 was used to assess the variation in volume per cavity where the sample fluid is $H_2O$. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

Sample receptacle with venting holes

| | A | B | C |
|---|---|---|---|
| R1 | | | |
| 1 | 71 | 83 | 88 |
| 2 | 79 | 89 | 88 |
| 3 | 82 | 89 | 87 |
| 4 | 87 | 89 | 87 |
| 5 | 91 | 88 | 95 |
| 6 | 91 | 92 | 92 |
| 7 | 96 | 91 | 93 |
| 8 | 84 | 86 | 94 |

| | Average | Std | CV |
|---|---|---|---|
| ul | 88 | 5 | 6.1% |

R2

| | A | B | C |
|---|---|---|---|
| 1 | 74 | 82 | 86 |
| 2 | 85 | 87 | 88 |
| 3 | 91 | 88 | 92 |
| 4 | 89 | 90 | 86 |
| 5 | 91 | 94 | 92 |
| 6 | 88 | 95 | 94 |

Sample receptacle with venting holes

| | A | B | C |
|---|---|---|---|
| 7 | 81 | 26 | 91 |
| 8 | 91 | 91 | 91 |

| | Average | Std | CV |
|---|---|---|---|
| ul | 86 | 13 | 15.5% |

R3

| | A | B | C |
|---|---|---|---|
| 1 | 94 | 90 | 89 |
| 2 | 85 | 93 | 87 |
| 3 | 83 | 85 | 77 |
| 4 | 89 | 28 | 92 |
| 5 | 90 | 93 | 90 |
| 6 | 93 | 88 | 90 |
| 7 | 89 | 88 | 94 |
| 8 | 92 | 89 | 90 |

| | Average | Std | CV |
|---|---|---|---|
| ul | 87 | 13 | 14.8% |

R4

| | A | B | C |
|---|---|---|---|
| 1 | 71 | 85 | 86 |
| 2 | 82 | 85 | 89 |
| 3 | 87 | 90 | 88 |
| 4 | 89 | 87 | 93 |
| 5 | 91 | 92 | 91 |
| 6 | 92 | 34 | 91 |
| 7 | 91 | 90 | 93 |
| 8 | 88 | 90 | 93 |

| | Average | Std | CV |
|---|---|---|---|
| ul | 86 | 12 | 13.7% |

R5

| | A | B | C |
|---|---|---|---|
| 1 | 77 | 84 | 86 |
| 2 | 84 | 89 | 83 |
| 3 | 89 | 86 | 91 |
| 4 | 92 | 89 | 90 |
| 5 | 90 | 89 | 93 |
| 6 | 85 | 81 | 98 |
| 7 | 89 | 95 | 91 |
| 8 | 92 | 91 | 91 |

| | Average | Std | CV |
|---|---|---|---|
| ul | 89 | 5 | 5.1% |

| | Overall average | Std | CV |
|---|---|---|---|
| ul | 87 | 10 | 11.9% |

Example 18

In this example a receptacle of the form shown in FIGS. 1 to 4 was used to assess the variation in volume per cavity where the sample fluid is H2O. The receptacle has 3 rows A to C and eight columns 1 to 8. A cylindrical vent hole having a diameter of 0.2 mm is provided in the base of each cavity. The liquid samples in each cavity were delivered into respective wells of a sample container. The five tests C1 to C5 show the volumes in each well in ul, the average volume in each cavity, the standard deviation (Std) and the coefficient of variation (CV) and at the end the Std and CV for all tests.

| Sample Container | | | |
|---|---|---|---|
| | A | B | C |
| C1 | | | |
| 1 | 84 | 89 | 64 |
| 2 | 85 | 91 | 83 |
| 3 | 90 | 84 | 90 |
| 4 | 91 | 88 | 90 |
| 5 | 90 | 90 | 90 |
| 6 | 74 | 95 | 91 |
| 7 | 91 | 88 | 91 |
| 8 | 95 | 91 | 93 |
| | Average | Std | CV |
| ul | 88 | 7 | 7.5% |
| C2 | | | |
| 1 | 35 | 86 | 70 |
| 2 | 90 | 88 | 86 |
| 3 | 89 | 91 | 88 |
| 4 | 92 | 94 | 88 |
| 5 | 91 | 95 | 92 |
| 6 | 92 | 95 | 91 |
| 7 | 96 | 96 | 85 |
| 8 | 90 | 90 | 86 |
| | Average | Std | CV |
| ul | 87 | 12 | 13.8% |
| C3 | | | |
| 1 | 89 | 84 | 76 |
| 2 | 88 | 89 | 86 |
| 3 | 89 | 94 | 90 |
| 4 | 90 | 92 | 90 |
| 5 | 90 | 95 | 93 |
| 6 | 92 | 94 | 91 |
| 7 | 92 | 96 | 95 |
| 8 | 92 | 92 | 92 |
| | Average | Std | CV |
| ul | 90 | 4 | 4.5% |
| C4 | | | |
| 1 | 90 | 84 | 76 |
| 2 | 88 | 90 | 83 |
| 3 | 90 | 93 | 89 |
| 4 | 91 | 89 | 60 |
| 5 | 91 | 94 | 92 |
| 6 | 90 | 90 | 90 |
| 7 | 90 | 96 | 91 |
| 8 | 90 | 97 | 92 |
| | Average | Std | CV |
| ul | 89 | 7 | 8.2% |
| C5 | | | |
| 1 | 78 | 83 | 74 |
| 2 | 89 | 93 | 86 |
| 3 | 88 | 94 | 90 |
| 4 | 91 | 95 | 90 |
| 5 | 89 | 97 | 93 |
| 6 | 90 | 95 | 90 |
| 7 | 92 | 96 | 96 |
| 8 | 91 | 90 | 92 |
| | Average | Std | CV |
| ul | 90 | 5 | 5.9% |
| Overall average | | Std | CV |
| ul | 89 | 8 | 8.6% |

Example 19

In this example a receptacle of the form shown in FIGS. 1 to 4 was used to assess the variation in volume per cavity where the sample fluid is H2O. The receptacle has 3 rows A to C and eight columns 1 to 8. The cavities have no vent hole. The five tests R1 to R5 show the volumes in each cavity in ul, the average volume in each cavity, the standard deviation (Std) and the coefficient of variation (CV) and at the end the Std and CV for all tests.

| Sample receptacle with closed venting holes | | | |
|---|---|---|---|
| | A | B | C |
| R1 | | | |
| 1 | 0 | 0 | 8 |
| 2 | 0 | 90 | 14 |
| 3 | 0 | 0 | 11 |
| 4 | 0 | 0 | 8 |
| 5 | 91 | 96 | 44 |
| 6 | 17 | 46 | 7 |
| 7 | 6 | 15 | 0 |
| 8 | 4 | 50 | 12 |
| | Average | Std | CV |
| ul | 22 | 30 | 140.4% |
| R2 | | | |
| 1 | 0 | 0 | 0 |
| 2 | 0 | 0 | 10 |
| 3 | 7 | 0 | 0 |
| 4 | 10 | 97 | 10 |
| 5 | 2 | 98 | 0 |
| 6 | 13 | 36 | 24 |
| 7 | 0 | 97 | 9 |
| 8 | 0 | 0 | 0 |
| | Average | Std | CV |
| ul | 17 | 31 | 183.0% |
| R3 | | | |
| 1 | 0 | 0 | 7 |
| 2 | 5 | 90 | 11 |
| 3 | 34 | 94 | 10 |
| 4 | 0 | 91 | 5 |
| 5 | 9 | 95 | 8 |
| 6 | 15 | 91 | 17 |

-continued

Sample receptacle with closed venting holes

|   | A | B | C |
|---|---|---|---|
| 7 | 10 | 58 | 11 |
| 8 | 7 | 0 | 0 |

|    | Average | Std | CV |
|----|---------|-----|-----|
| ul | 28 | 35 | 126.4% |

R4

|   | A | B | C |
|---|---|---|---|
| 1 | 0 | 0 | 6 |
| 2 | 0 | 0 | 9 |
| 3 | 9 | 0 | 7 |
| 4 | 4 | 93 | 11 |
| 5 | 2 | 93 | 10 |
| 6 | 7 | 94 | 21 |
| 7 | 14 | 0 | 16 |
| 8 | 7 | 0 | 7 |

|    | Average | Std | CV |
|----|---------|-----|-----|
| ul | 17 | 29 | 171.7% |

R5

|   | A | B | C |
|---|---|---|---|
| 1 | 0 | 0 | 0 |
| 2 | 0 | 90 | 10 |
| 3 | 2 | 77 | 6 |
| 4 | 3 | 96 | 4 |
| 5 | 3 | 94 | 11 |
| 6 | 7 | 89 | 5 |
| 7 | 0 | 96 | 7 |
| 8 | 2 | 98 | 5 |

|    | Average | Std | CV |
|----|---------|-----|-----|
| ul | 29 | 40 | 136.5% |

|    | Overall average | Std | CV |
|----|-----------------|-----|-----|
| ul | 23 | 34 | 149.9% |

Example 20

In this example a receptacle of the form shown in FIGS. 1 to 4 was used to assess the variation in volume per cavity where the sample fluid is Ethanol. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

Sample receptacle with venting holes

|   | A | B | C |
|---|---|---|---|
| R1 |   |   |   |
| 1 | 44 | 71 | 69 |
| 2 | 66 | 69 | 68 |
| 3 | 66 | 64 | 50 |
| 4 | 67 | 60 | 20 |
| 5 | 66 | 52 | 11 |
| 6 | 67 | 42 | 7 |

-continued

Sample receptacle with venting holes

|   | A | B | C |
|---|---|---|---|
| 7 | 68 | 13 | 6 |
| 8 | 66 | 6 | 5 |

|    | Average | Std | CV |
|----|---------|-----|-----|
| ul | 47 | 25 | 53.6% |

R2

|   | A | B | C |
|---|---|---|---|
| 1 | 60 | 72 | 69 |
| 2 | 67 | 67 | 65 |
| 3 | 66 | 64 | 53 |
| 4 | 65 | 64 | 38 |
| 5 | 68 | 58 | 32 |
| 6 | 68 | 55 | 27 |
| 7 | 68 | 41 | 18 |
| 8 | 68 | 30 | 6 |

|    | Average | Std | CV |
|----|---------|-----|-----|
| ul | 54 | 18 | 34.3% |

R3

|   | A | B | C |
|---|---|---|---|
| 1 | 53 | 68 | 75 |
| 2 | 66 | 76 | 72 |
| 3 | 67 | 63 | 60 |
| 4 | 65 | 64 | 53 |
| 5 | 68 | 57 | 44 |
| 6 | 66 | 58 | 36 |
| 7 | 68 | 44 | 27 |
| 8 | 68 | 35 | 10 |

|    | Average | Std | CV |
|----|---------|-----|-----|
| ul | 57 | 16 | 28.3% |

R4

|   | A | B | C |
|---|---|---|---|
| 1 | 47 | 66 | 61 |
| 2 | 61 | 62 | 56 |
| 3 | 64 | 61 | 48 |
| 4 | 65 | 62 | 38 |
| 5 | 65 | 54 | 25 |
| 6 | 67 | 51 | 21 |
| 7 | 66 | 37 | 11 |
| 8 | 66 | 27 | 6 |

|    | Average | Std | CV |
|----|---------|-----|-----|
| ul | 49 | 18 | 37.3% |

R5

|   | A | B | C |
|---|---|---|---|
| 1 | 62 | 64 | 59 |
| 2 | 67 | 62 | 56 |
| 3 | 67 | 62 | 52 |
| 4 | 67 | 65 | 36 |
| 5 | 69 | 61 | 27 |
| 6 | 66 | 58 | 27 |
| 7 | 70 | 44 | 16 |
| 8 | 67 | 37 | 7 |

|    | Average | Std | CV |
|----|---------|-----|-----|
| ul | 53 | 18 | 33.7% |

|    | Overall average | Std | CV |
|----|-----------------|-----|-----|
| ul | 52 | 20 | 38.0% |

Example 21

In this example a receptacle of the form shown in FIGS. 1 to 4 was used to assess the variation in volume per cavity where the sample fluid is Ethanol. The receptacle has 3 rows A to C and eight columns 1 to 8. A cylindrical vent hole having a diameter of 0.2 mm is provided in the base of each cavity. The liquid samples in each cavity were delivered into respective wells of a sample container. The five tests C1 to C5 show the volumes in each well in ul, the average volume in each cavity, the standard deviation (Std) and the coefficient of variation (CV) and at the end the Std and CV for all tests.

| Sample Container | | | |
|---|---|---|---|
| | A | B | C |
| C1 | | | |
| 1 | 60 | 59 | 37 |
| 2 | 67 | 69 | 53 |
| 3 | 68 | 69 | 53 |
| 4 | 63 | 66 | 55 |
| 5 | 60 | 64 | 66 |
| 6 | 62 | 68 | 60 |
| 7 | 61 | 65 | 58 |
| 8 | 62 | 64 | 60 |
| | Average | Std | CV |
| ul | 61 | 7 | 11.1% |
| C2 | | | |
| 1 | 54 | 67 | 34 |
| 2 | 54 | 62 | 41 |
| 3 | 49 | 68 | 50 |
| 4 | 67 | 65 | 62 |
| 5 | 68 | 70 | 61 |
| 6 | 65 | 68 | 66 |
| 7 | 70 | 72 | 65 |
| 8 | 69 | 70 | 56 |
| | Average | Std | CV |
| ul | 61 | 10 | 15.7% |
| C3 | | | |
| 1 | 65 | 66 | 29 |
| 2 | 64 | 69 | 42 |
| 3 | 68 | 69 | 40 |
| 4 | 66 | 68 | 49 |
| 5 | 61 | 63 | 63 |
| 6 | 64 | 66 | 67 |
| 7 | 56 | 66 | 52 |
| 8 | 67 | 66 | 46 |
| | Average | Std | CV |
| ul | 60 | 11 | 17.9% |
| C4 | | | |
| 1 | 60 | 64 | 25 |
| 2 | 52 | 55 | 42 |
| 3 | 53 | 56 | 52 |
| 4 | 61 | 65 | 51 |
| 5 | 61 | 66 | 67 |
| 6 | 63 | 66 | 36 |
| 7 | 64 | 62 | 33 |
| 8 | 60 | 63 | 37 |
| | Average | Std | CV |
| ul | 55 | 12 | 21.2% |
| C5 | | | |
| 1 | 64 | 66 | 17 |
| 2 | 64 | 69 | 42 |
| 3 | 67 | 68 | 48 |
| 4 | 68 | 61 | 45 |
| 5 | 61 | 63 | 59 |
| 6 | 65 | 59 | 50 |
| 7 | 66 | 66 | 38 |
| 8 | 65 | 57 | 54 |
| | Average | Std | CV |
| ul | 58 | 12 | 20.9% |
| | Overall average | Std | CV |
| ul | 59 | 11 | 18.0% |

Example 22

In this example a receptacle of the form shown in FIGS. 1 to 4 was used to assess the variation in volume per cavity where the sample fluid is Ethanol. The receptacle has 3 rows A to C and eight columns 1 to 8. The cavities have no vent hole. The five tests R1 to R5 show the volumes in each cavity in ul, the average volume in each cavity, the standard deviation (Std) and the coefficient of variation (CV) and at the end the Std and CV for all tests.

| Sample receptacle with closed venting holes | | | |
|---|---|---|---|
| | A | B | C |
| R1 | | | |
| 1 | 49 | 70 | 72 |
| 2 | 65 | 70 | 71 |
| 3 | 70 | 72 | 73 |
| 4 | 69 | 71 | 72 |
| 5 | 69 | 72 | 72 |
| 6 | 66 | 72 | 72 |
| 7 | 70 | 71 | 73 |
| 8 | 70 | 71 | 69 |
| | Average | Std | CV |
| ul | 70 | 5 | 6.8% |
| R2 | | | |
| 1 | 56 | 71 | 70 |
| 2 | 66 | 72 | 73 |
| 3 | 69 | 72 | 73 |
| 4 | 70 | 71 | 73 |
| 5 | 70 | 71 | 71 |
| 6 | 68 | 67 | 71 |

| Sample receptacle with closed venting holes | | |
|---|---|---|
| A | B | C |
| 7 | 70 | 71 | 70 |
| 8 | 70 | 73 | 71 |

| | Average | Std | CV |
|---|---|---|---|
| ul | 70 | 3 | 4.9% |

R3

| | A | B | C |
|---|---|---|---|
| 1 | 64 | 71 | 70 |
| 2 | 66 | 70 | 73 |
| 3 | 67 | 72 | 73 |
| 4 | 69 | 70 | 71 |
| 5 | 68 | 72 | 70 |
| 6 | 67 | 70 | 72 |
| 7 | 69 | 70 | 71 |
| 8 | 70 | 73 | 70 |

| | Average | Std | CV |
|---|---|---|---|
| ul | 70 | 2 | 3.2% |

R4

| | A | B | C |
|---|---|---|---|
| 1 | 49 | 69 | 70 |
| 2 | 67 | 70 | 70 |
| 3 | 68 | 71 | 73 |
| 4 | 68 | 68 | 69 |
| 5 | 69 | 69 | 70 |
| 6 | 70 | 70 | 70 |
| 7 | 70 | 72 | 66 |
| 8 | 69 | 71 | 70 |

| | Average | Std | CV |
|---|---|---|---|
| ul | 69 | 4 | 6.3% |

R5

| | A | B | C |
|---|---|---|---|
| 1 | 62 | 69 | 66 |
| 2 | 67 | 68 | 66 |
| 3 | 68 | 68 | 71 |
| 4 | 68 | 70 | 68 |
| 5 | 67 | 71 | 70 |
| 6 | 70 | 72 | 74 |
| 7 | 69 | 74 | 74 |
| 8 | 70 | 73 | 70 |

| | Average | Std | CV |
|---|---|---|---|
| ul | 69 | 3 | 4.1% |

| | Overall average | Std | CV |
|---|---|---|---|
| ul | 70 | 4 | 5.3% |

Example 23

In this example a receptacle of the form shown in FIGS. 1 to 4 was used to assess the variation in volume per cavity where the sample fluid is medium chain triglyceride Miglyol 812. The receptacle has 3 rows A to C and eight columns 1 to 8. A cylindrical vent hole having a diameter of 0.2 mm is provided in the base of each cavity. The five tests R1 to R5 show the volumes in each cavity in ul, the average volume in each cavity, the standard deviation (Std) and the coefficient of variation (CV) and at the end the Std and CV for all tests.

| Sample receptacle with venting holes | | |
|---|---|---|
| A | B | C |

R1

| | A | B | C |
|---|---|---|---|
| 1 | 72 | 78 | 78 |
| 2 | 76 | 78 | 73 |
| 3 | 65 | 79 | 74 |
| 4 | 72 | 86 | 67 |
| 5 | 74 | 80 | 62 |
| 6 | 79 | 81 | 60 |
| 7 | 72 | 75 | 54 |
| 8 | 75 | 74 | 73 |

| | Average | Std | CV |
|---|---|---|---|
| ul | 73 | 7 | 9.7% |

R2

| | A | B | C |
|---|---|---|---|
| 1 | 60 | 76 | 70 |
| 2 | 77 | 77 | 74 |
| 3 | 72 | 83 | 75 |
| 4 | 73 | 71 | 71 |
| 5 | 67 | 80 | 63 |
| 6 | 67 | 87 | 64 |
| 7 | 79 | 68 | 45 |
| 8 | 68 | 56 | 15 |

| | Average | Std | CV |
|---|---|---|---|
| ul | 68 | 14 | 20.7% |

R3

| | A | B | C |
|---|---|---|---|
| 1 | 64 | 80 | 56 |
| 2 | 61 | 97 | 69 |
| 3 | 70 | 95 | 55 |
| 4 | 71 | 75 | 63 |
| 5 | 79 | 75 | 61 |
| 6 | 70 | 70 | 74 |
| 7 | 70 | 74 | 62 |
| 8 | 76 | 70 | 35 |

| | Average | Std | CV |
|---|---|---|---|
| ul | 70 | 12 | 17.6% |

R4

| | A | B | C |
|---|---|---|---|
| 1 | 76 | 65 | 46 |
| 2 | 62 | 50 | 23 |
| 3 | 53 | 85 | 30 |
| 4 | 75 | 44 | 28 |
| 5 | 67 | 53 | 11 |
| 6 | 48 | 49 | 10 |
| 7 | 72 | 44 | 5 |
| 8 | 78 | 30 | 9 |

| | Average | Std | CV |
|---|---|---|---|
| ul | 46 | 23 | 50.4% |

R5

| | A | B | C |
|---|---|---|---|
| 1 | 73 | 77 | 72 |
| 2 | 75 | 86 | 71 |
| 3 | 68 | 86 | 79 |
| 4 | 78 | 78 | 72 |
| 5 | 74 | 85 | 64 |
| 6 | 80 | 89 | 56 |

-continued

| Sample receptacle with venting holes | | | |
|---|---|---|---|
| | A | B | C |
| 7 | 69 | 81 | 44 |
| 8 | 71 | 70 | 42 |
| | Average | Std | CV |
| ul | 73 | 12 | 15.9% |
| | Overall average | Std | CV |
| ul | 66 | 18 | 26.9% |

Example 24

In this example a receptacle of the form shown in FIGS. 1 to 4 was used to assess the variation in volume per cavity where the sample fluid is medium chain triglyceride Miglyol 812. The receptacle has 3 rows A to C and eight columns 1 to 8. A cylindrical vent hole having a diameter of 0.2 mm is provided in the base of each cavity. The liquid samples in each cavity were delivered into respective wells of a sample container. The five tests C1 to C5 show the volumes in each well in ul, the average volume in each cavity, the standard deviation (Std) and the coefficient of variation (CV) and at the end the Std and CV for all tests.

| Sample Container | | | |
|---|---|---|---|
| | A | B | C |
| C1 | | | |
| 1 | 50 | 50 | 42 |
| 2 | 55 | 54 | 55 |
| 3 | 50 | 48 | 48 |
| 4 | 50 | 53 | 56 |
| 5 | 49 | 59 | 57 |
| 6 | 50 | 53 | 49 |
| 7 | 50 | 53 | 53 |
| 8 | 57 | 64 | 74 |
| | Average | Std | CV |
| ul | 53 | 6 | 11.5% |
| C2 | | | |
| 1 | 43 | 62 | 22 |
| 2 | 44 | 65 | 12 |
| 3 | 40 | 71 | 24 |
| 4 | 55 | 75 | 27 |
| 5 | 49 | 66 | 9 |
| 6 | 51 | 64 | 48 |
| 7 | 60 | 62 | 52 |
| 8 | 61 | 63 | 63 |
| | Average | Std | CV |
| ul | 50 | 18 | 36.7% |
| C3 | | | |
| 1 | 49 | 45 | 41 |
| 2 | 42 | 43 | 67 |
| 3 | 43 | 57 | 64 |
| 4 | 49 | 63 | 63 |
| 5 | 50 | 62 | 62 |
| 6 | 53 | 55 | 56 |

-continued

| Sample Container | | | |
|---|---|---|---|
| | A | B | C |
| 7 | 68 | 53 | 52 |
| 8 | 65 | 63 | 57 |
| | Average | Std | CV |
| ul | 55 | 8 | 15.1% |
| C4 | | | |
| 1 | 40 | 50 | 45 |
| 2 | 48 | 43 | 45 |
| 3 | 45 | 46 | 47 |
| 4 | 46 | 46 | 53 |
| 5 | 51 | 48 | 50 |
| 6 | 45 | 52 | 51 |
| 7 | 42 | 48 | 54 |
| 8 | 58 | 55 | 63 |
| | Average | Std | CV |
| ul | 49 | 5 | 10.6% |
| C5 | | | |
| 1 | 37 | 50 | 59 |
| 2 | 49 | 54 | 63 |
| 3 | 46 | 65 | 60 |
| 4 | 75 | 63 | 67 |
| 5 | 60 | 69 | 54 |
| 6 | 64 | 55 | 58 |
| 7 | 60 | 46 | 69 |
| 8 | 70 | 66 | 58 |
| | Average | Std | CV |
| ul | 59 | 9 | 14.9% |
| | Overall average | Std | CV |
| ul | 53 | 11 | 20.8% |

Example 25

In this example a receptacle of the form shown in FIGS. 1 to 4 was used to assess the variation in volume per cavity where the sample fluid is medium chain triglyceride Miglyol 812. The receptacle has 3 rows A to C and eight columns 1 to 8. The cavities have no vent hole. The five tests R1 to R5 show the volumes in each cavity in ul, the average volume in each cavity, the standard deviation (Std) and the coefficient of variation (CV) and at the end the Std and CV for all tests.

| Sample receptacle with closed venting holes | | | |
|---|---|---|---|
| | A | B | C |
| R1 | | | |
| 1 | 75 | 69 | 72 |
| 2 | 67 | 73 | 74 |
| 3 | 71 | 76 | 73 |
| 4 | 60 | 75 | 75 |
| 5 | 69 | 75 | 81 |
| 6 | 67 | 80 | 79 |

-continued

Sample receptacle with closed venting holes

|   | A | B | C |
|---|---|---|---|
| 7 | 69 | 83 | 84 |
| 8 | 67 | 80 | 81 |

|  | Average | Std | CV |
|---|---|---|---|
| ul | 74 | 6 | 7.9% |

R2

|   | | | |
|---|---|---|---|
| 1 | 57 | 79 | 76 |
| 2 | 69 | 76 | 78 |
| 3 | 75 | 78 | 79 |
| 4 | 70 | 85 | 83 |
| 5 | 76 | 79 | 87 |
| 6 | 75 | 82 | 85 |
| 7 | 70 | 83 | 77 |
| 8 | 70 | 77 | 87 |

|  | Average | Std | CV |
|---|---|---|---|
| ul | 77 | 7 | 8.6% |

R3

|   | | | |
|---|---|---|---|
| 1 | 81 | 76 | 74 |
| 2 | 70 | 80 | 80 |
| 3 | 76 | 88 | 77 |
| 4 | 72 | 87 | 80 |
| 5 | 76 | 92 | 85 |
| 6 | 72 | 83 | 82 |
| 7 | 70 | 88 | 82 |
| 8 | 79 | 89 | 77 |

|  | Average | Std | CV |
|---|---|---|---|
| ul | 80 | 6 | 7.6% |

R4

|   | | | |
|---|---|---|---|
| 1 | 79 | 68 | 78 |
| 2 | 70 | 80 | 75 |
| 3 | 70 | 85 | 85 |
| 4 | 69 | 85 | 80 |
| 5 | 71 | 87 | 87 |
| 6 | 76 | 84 | 81 |
| 7 | 70 | 78 | 83 |
| 8 | 79 | 86 | 78 |

|  | Average | Std | CV |
|---|---|---|---|
| ul | 79 | 6 | 7.7% |

R5

|   | | | |
|---|---|---|---|
| 1 | 72 | 83 | 82 |
| 2 | 74 | 84 | 79 |
| 3 | 74 | 82 | 81 |
| 4 | 74 | 86 | 85 |
| 5 | 71 | 81 | 83 |
| 6 | 77 | 85 | 83 |
| 7 | 73 | 88 | 83 |
| 8 | 78 | 88 | 77 |

|  | Average | Std | CV |
|---|---|---|---|
| ul | 80 | 5 | 6.2% |

|  | Overall average | Std | CV |
|---|---|---|---|
| ul | 78 | 6 | 8.1% |

The invention claimed is:

1. A sample analysis kit comprising:
   a. a sample receptacle including a plurality of receptacle wells, each receptacle well having a mouth at one end and one or more apertures in its base and one or more receptacle walls surrounding and extending above the wells;
   b. a sample container including one or more container wells each having a mouth dimensioned to mate with the base of a respective receptacle well; and
   c. a plunger assembly including one or more pistons, wherein each of the one or more pistons is dimensioned to advance within a respective receptacle well so as to eject liquid within the receptacle well out of each aperture.

2. A sample analysis kit as claimed in claim 1 wherein a plurality of apertures are provided in the base of each receptacle well.

3. A sample analysis kit as claimed in claim 1 in which each receptacle well is mated with the mouth of each container well.

4. A sample analysis kit as claimed in claim 3 wherein a reactant is provided within each container well.

5. A sample analysis kit as claimed in claim 4 wherein different concentrations of at least one reactant are provided in at least some container wells.

6. A sample analysis kit as claimed in claim 4 wherein at least one reactant is an antibiotic.

7. A sample analysis kit as claimed in claim 4 wherein at least some container wells include a dye.

8. A sample analysis kit as claimed in claim 4 wherein each container well includes a bacteria culture media.

9. A sample analysis kit as claimed in claim 1 wherein each receptacle well has a diameter of between 1 mm and 15 mm.

10. A sample analysis kit as claimed in claim 1 wherein each receptacle well height is between 0.5 mm to 20 mm.

11. A sample analysis kit as claimed in claim 1 wherein the cross-sectional area of each receptacle well mouth is less than 100 $mm^2$.

12. A sample analysis kit as claimed in claim 1 wherein the aperture functions as a gas vent providing a gas escape pathway from the base of each receptacle well.

13. A sample analysis kit as claimed in claim 12 wherein the gas vent has an area of less than 1 $mm^2$.

14. A sample analysis kit as claimed in claim 1 wherein the one or more receptacle wall is greater than 1 mm higher than the one or more receptacle well mouths.

15. A sample analysis kit comprising:
   a. a sample receptacle including a plurality of receptacle wells, each receptacle well having a mouth at one end and one or more apertures in its base, each mouth being open to a region above the receptacle wells, the sample receptacle further including one or more perimeter receptacle walls surrounding and extending above the plurality of receptacle wells;
   b. a sample container including one or more container wells each having a mouth dimensioned to mate with the base of a respective receptacle well; and
   c. a plunger assembly including one or more pistons dimensioned to advance within a respective receptacle well so as to eject liquid within the receptacle well out of each aperture.

16. A sample analysis kit as claimed in claim 15, wherein each receptacle well is mated with the mouth of each container well.

17. A sample analysis kit as claimed in claim 15, wherein one or more of the group consisting of a reactant, a dye, and a bacteria culture medium is provided within each of the container wells.

18. A sample analysis kit as claimed in claim 17, wherein different concentrations of at least one reactant are provided in at least some container wells.

19. A sample analysis kit as claimed in claim 17, wherein at least one reactant is an antibiotic.

* * * * *